United States Patent
Wang et al.

(10) Patent No.: US 12,091,385 B2
(45) Date of Patent: Sep. 17, 2024

(54) PYRIDINYLCYANOGUANIDINE DERIVATIVE AND USE THEREOF

(71) Applicants: Zheming Wang, Zhejiang (CN); Rushi Biotech (Hangzhou) Co., Ltd, Zhejiang (CN)

(72) Inventors: Zheming Wang, Zhejiang (CN); Hao Tan, Zhejiang (CN)

(73) Assignees: Zheming Wang, Hangzhou (CN); Rushi Biotech (Hangzhou) Co., Ltd, Hangzhou (CN)

( * ) Notice: Subject to any disclaimer, the term of this patent is extended or adjusted under 35 U.S.C. 154(b) by 0 days.

(21) Appl. No.: 18/383,896

(22) Filed: Oct. 25, 2023

(65) Prior Publication Data

US 2024/0067607 A1 Feb. 29, 2024

Related U.S. Application Data

(63) Continuation of application No. 18/080,723, filed on Dec. 13, 2022, now Pat. No. 11,873,284.

(30) Foreign Application Priority Data

Dec. 22, 2021 (CN) .......................... 202111580925.4

(51) Int. Cl.
| | |
|---|---|
| *C07D 401/12* | (2006.01) |
| *C07D 213/75* | (2006.01) |
| *C07D 405/12* | (2006.01) |
| *C07D 409/14* | (2006.01) |

(52) U.S. Cl.
CPC ......... *C07D 213/75* (2013.01); *C07D 401/12* (2013.01); *C07D 405/12* (2013.01); *C07D 409/14* (2013.01)

(58) Field of Classification Search
CPC ................ C07D 401/12; C07D 405/14; C07D 409/14
See application file for complete search history.

(56) References Cited

FOREIGN PATENT DOCUMENTS

WO WO-2018024907 A1 * 2/2018 .............. A61P 35/00

* cited by examiner

*Primary Examiner* — Laura L Stockton

(57) ABSTRACT

The present invention discloses a pyridinylcyanoguanidine derivative or a pharmaceutically acceptable salt thereof, which is useful as an NAMPT inhibitor, and useful as a potential agent for the chemotherapy of a variety of diseases associated with abnormal $NAD^+$ expression. The pyridinylcyanoguanidine derivative has a parent structure including cyanoguanidine attached to piperazine or pyrrolidine by an intermediate aliphatic chain, to which a side arylformyl (or heterocyclylformyl) group and pyridinyl (or substituted pyridinyl) group are attached. This structure comes from the structural optimization of FK866, a high-efficiency NAMPT inhibitor. In the structure, the substituted formyl piperazine and substituted formyl pyrrolidine are the further optimizations on the basis of FK866, which strengthens the interaction with NAMPT. The introduction of cyanoguanidine structure not only further enhances the affinity with NAMPT, but also improves the disadvantage of poor water solubility of FK866, which is more conducive to the subsequent drug test.

2 Claims, No Drawings

PYRIDINYLCYANOGUANIDINE DERIVATIVE AND USE THEREOF

CROSS-REFERENCE TO RELATED APPLICATION

The present application is a continuation application of U.S. patent application Ser. No. 18/080,723 filed on Dec. 13, 2022, which claims priority from Chinese Patent Application No. 202111580925.4 filed on Dec. 22, 2021, the contents of which are incorporated herein by reference in their entirety.

TECHNICAL FIELD

The present invention relates to a guanidine compound and use thereof, and particularly to a pyridinylcyanoguanidine derivative and use thereof.

BACKGROUND

The metabolism in tumor cells is obviously different from that in normal cells. The tumor cells have high glycolytic ability and energy consumption for rapid division, proliferation and invasion. In this process, the tumor cells have a great demand for NAD$^+$. NAD$^+$ in tumor cells is mainly synthesized through the NAD$^+$ salvage pathway, in which NAMPT is a key rate-limiting enzyme in the salvage pathway. Therefore, inhibiting NAMPT can reduce the level of NAD$^+$ in tumor cells, thereby finally inducing the death of tumor cells.

Recent studies have confirmed that inhibiting the activity of NAMPT by an NAMPT inhibitor can significantly inhibit the proliferation of tumor cells in vitro and the growth of tumors in vivo. The expression of NAMPT and Sirt2 in primary acute myeloid leukemia cells increases significantly, and the specific inhibition of NAMPT or Sirt2 expression can inhibit the cell proliferation and induce the apoptosis of acute myeloid leukemia cells and primitive cells. As can be seen from the above research, NAMPT, as a new anti-tumor target, has received more and more attention from researchers, and NAMPT inhibitors, as a new generation of potential broad-spectrum anticancer drugs, have also become a hot spot in the research of anticancer drugs.

SUMMARY

To solve the disadvantages in the prior art, an object of the present invention is to provide a pyridinylcyanoguanidine derivative and use thereof.

The following technical solutions are adopted in the present invention.

The present invention provides a pyridinylcyanoguanidine derivative of Formula (I) or Formula (II), or a pharmaceutically acceptable salt thereof:

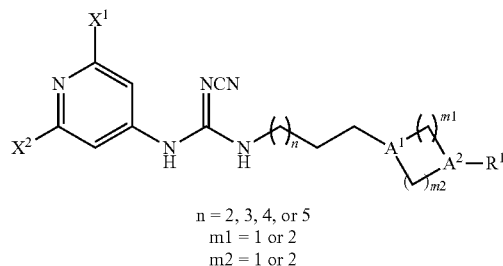

n = 2, 3, 4, or 5
m1 = 1 or 2
m2 = 1 or 2

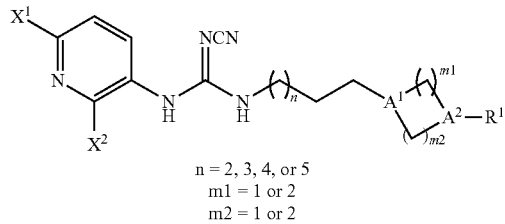

n = 2, 3, 4, or 5
m1 = 1 or 2
m2 = 1 or 2 where R$^1$ is arylformyl or heterocyclylformyl, in which the aryl or heterocyclyl is optionally mono- or poly substituted;
X$^1$ is hydrogen, fluoro, chloro, bromo, iodo or hydroxyl;
X$^2$ is hydrogen, fluoro, chloro, bromo, iodo or hydroxyl;
A$^1$ is carbon or nitrogen; and
A$^2$ is carbon or nitrogen.

The present invention provides a pyridinylcyanoguanidine derivative of Formula (III), Formula (IV), Formula (V) or Formula (VI), or a pharmaceutically acceptable salt thereof:

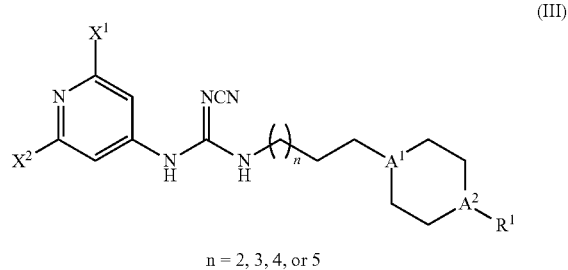

n = 2, 3, 4, or 5

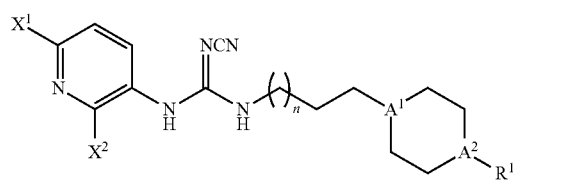

n = 2, 3, 4, or 5

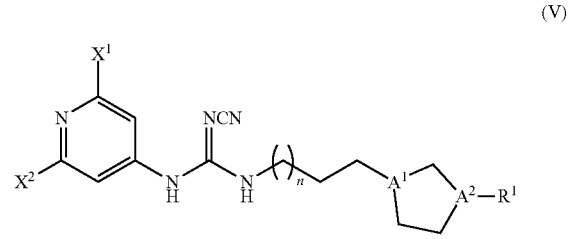

n = 2, 3, 4, or 5

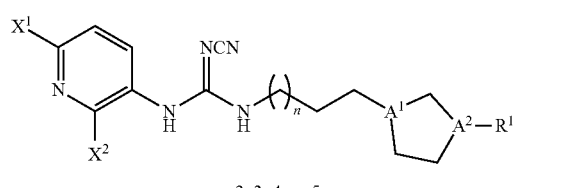

n = 2, 3, 4, or 5 where $R^1$ is arylformyl or heterocyclylformyl, in which the aryl or heterocyclyl is optionally mono- or polysubstituted;
$X^1$ is hydrogen, fluoro, chloro, bromo, iodo or hydroxyl;
$X^2$ is hydrogen, fluoro, chloro, bromo, iodo or hydroxyl;
$A^1$ is carbon or nitrogen; and
$A^2$ is carbon or nitrogen.

The present invention provides a pyridinylcyanoguanidine derivative of Formula (VII), Formula (VIII), Formula (IX) or Formula (X), or a pharmaceutically acceptable salt thereof:

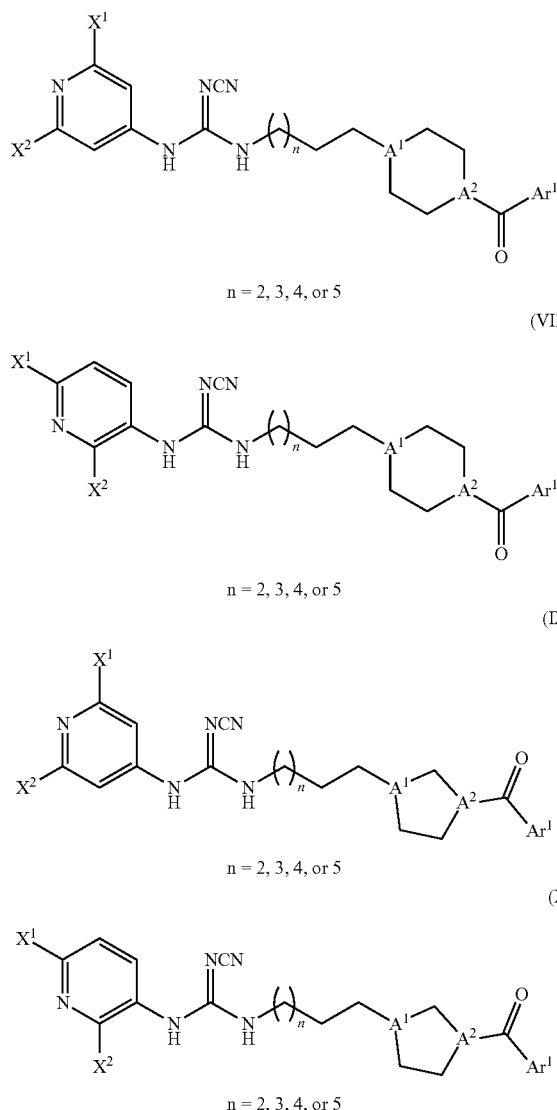

(VII)

n = 2, 3, 4, or 5

(VIII)

n = 2, 3, 4, or 5

(IX)

n = 2, 3, 4, or 5

(X)

n = 2, 3, 4, or 5 where $X^1$ is hydrogen, fluoro, chloro, bromo, iodo or hydroxyl;
$X^2$ is hydrogen, fluoro, chloro, bromo, iodo or hydroxyl;
$A^1$ is carbon or nitrogen;
$A^2$ is carbon or nitrogen; and
$Ar^1$ is a heteroatom containing cyclic alkyl or an aromatic ring system, including a five-membered heterocycloalkyl group, a six-membered heterocycloalkyl group, phenyl, heteroaryl, or benzoheterocylcyl, which is optionally mono-, di-, or trisubstituted, with a substituent including $C_1$-$C_3$ alkyl, $C_1$-$C_3$ alkoxy or hydroxyl.

The present invention provides a pyridinylcyanoguanidine derivative of Formula (XI), Formula (XII), Formula (XIII) or Formula (XIV), or a pharmaceutically acceptable salt thereof:

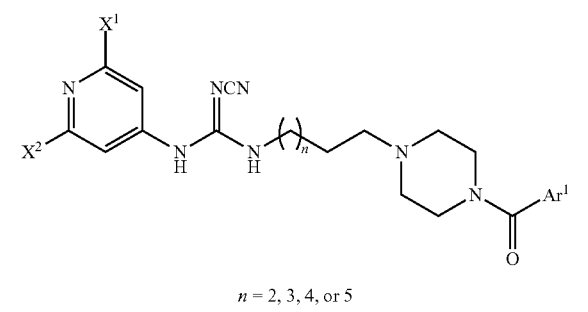

(XI)

n = 2, 3, 4, or 5

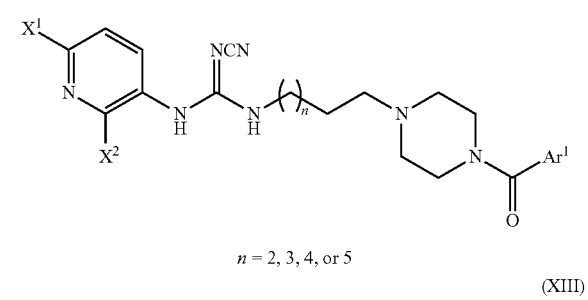

(XII)

n = 2, 3, 4, or 5

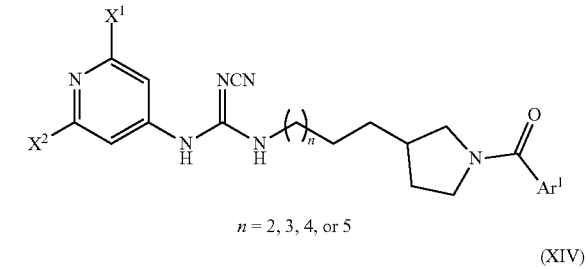

(XIII)

n = 2, 3, 4, or 5

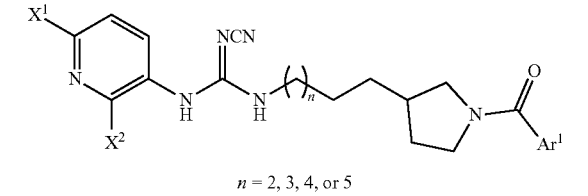

(XIV)

n = 2, 3, 4, or 5 where $X^1$ is hydrogen, fluoro, chloro, bromo, iodo or hydroxyl;
$X^2$ is hydrogen, fluoro, chloro, bromo, iodo or hydroxyl; and
$Ar^1$ is a heteroatom containing cyclic alkyl or an aromatic ring system, including a five-membered heterocycloalkyl group, a six-membered heterocycloalkyl group, phenyl, heteroaryl, or benzoheterocylcyl, which is optionally mono-, di-, or trisubstituted, with a substituent including $C_1$-$C_3$ alkyl, $C_1$-$C_3$ alkoxy or hydroxyl.

The present invention provides a pyridinylcyanoguanidine derivative of Formula (XV), Formula (XVI), Formula (XVII) or Formula (XVIII), or a pharmaceutically acceptable salt thereof:

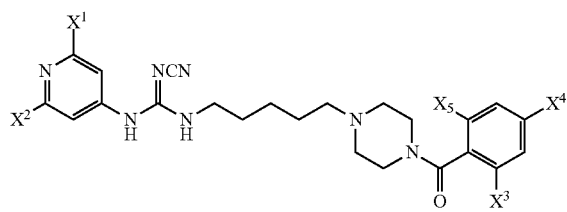
(XV)

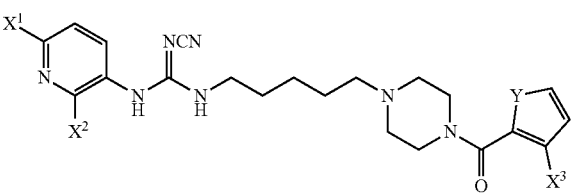
(XX)

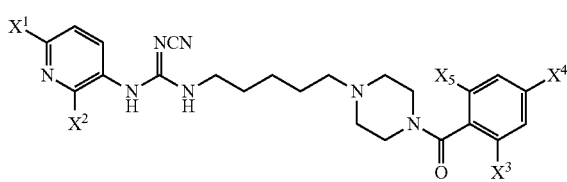
(XVI)

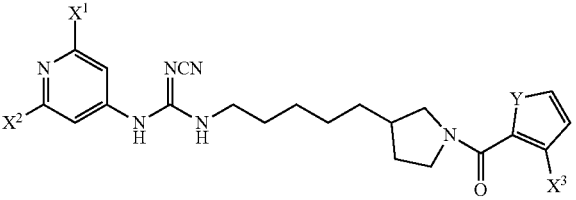
(XXI)

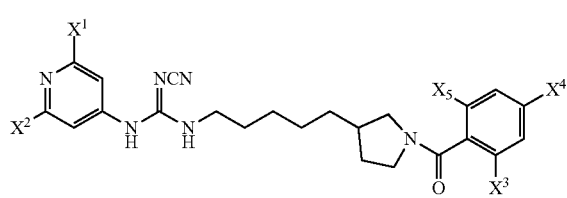
(XVII)

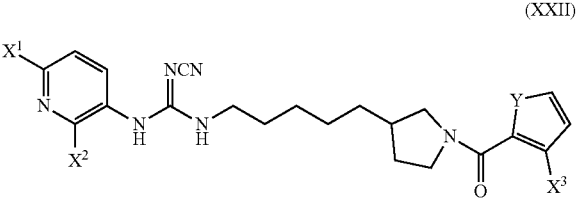
(XXII)

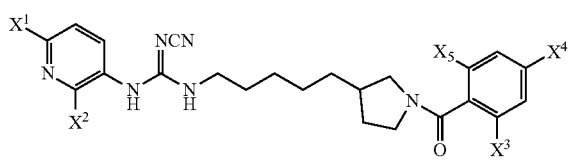
(XVIII)

where $X^1$ is hydrogen, fluoro, chloro, bromo, iodo or hydroxyl;

$X^2$ is hydrogen, fluoro, chloro, bromo, iodo or hydroxyl;

$X^3$ is hydrogen, fluoro, chloro, bromo, iodo or hydroxyl; and

Y is a heteroatom, including nitrogen, oxygen, or sulfur.

The present invention provides a pyridinylcyanoguanidine derivative of Formula (XXIII), Formula (XXIV), Formula (XXV) or Formula (XXVI), or a pharmaceutically acceptable salt thereof:

where $X^1$ is hydrogen, fluoro, chloro, bromo, iodo or hydroxyl;

$X^2$ is hydrogen, fluoro, chloro, bromo, iodo or hydroxyl;

$X^3$ is hydrogen, hydroxyl, $C_1$-$C_3$ alkyl or $C_1$-$C_3$ alkoxy;

$X^4$ is hydrogen, hydroxyl, $C_1$-$C_3$ alkyl or $C_1$-$C_3$ alkoxy; and $X^5$ is hydrogen, hydroxyl, $C_1$-$C_3$ alkyl or $C_1$-$C_3$ alkoxy.

The present invention provides a pyridinylcyanoguanidine derivative of Formula (XIX), Formula (XX), Formula (XXI) or Formula (XXII), or a pharmaceutically acceptable salt thereof:

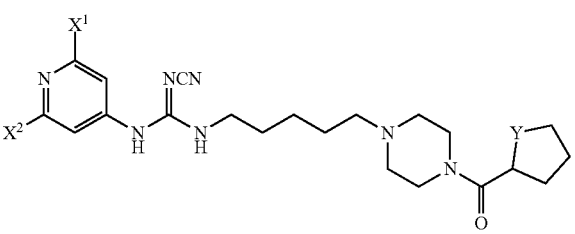
(XXIII)

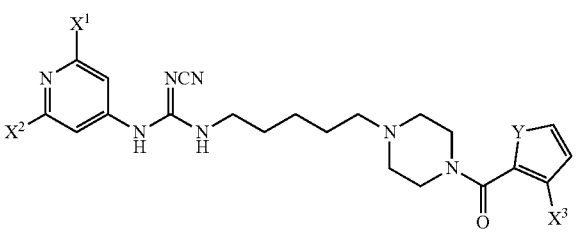
(XIX)

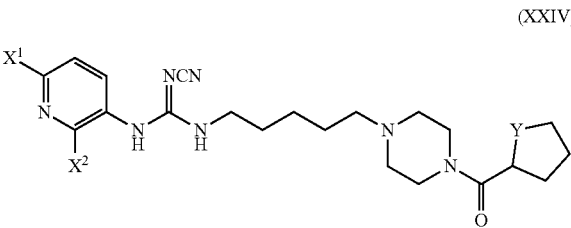
(XXIV)

-continued

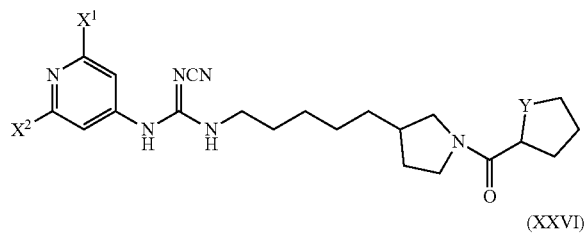
(XXV)

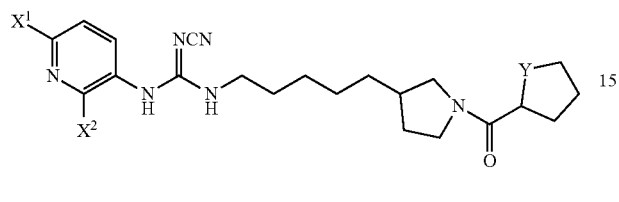
(XXVI)

where $X^1$ is hydrogen, fluoro, chloro, bromo, iodo or hydroxyl;
$X^2$ is hydrogen, fluoro, chloro, bromo, iodo or hydroxyl; and
Y is a heteroatom, including nitrogen, oxygen, or sulfur.

The present invention provides a pyridinylcyanoguanidine derivative of Formula (XXVII), Formula (XXVIII), Formula (XXIX) or Formula (XXX), or a pharmaceutically acceptable salt thereof:

where $X^1$ is hydrogen, fluoro, chloro, bromo, iodo or hydroxyl;
$X^2$ is hydrogen, fluoro, chloro, bromo, iodo or hydroxyl;
$X^3$ is hydrogen, hydroxyl, $C_1$-$C_3$ alkyl or $C_1$-$C_3$ alkoxy;
$X^4$ is hydrogen, hydroxyl, $C_1$-$C_3$ alkyl or $C_1$-$C_3$ alkoxy; and
$X^5$ is hydrogen, hydroxyl, $C_1$-$C_3$ alkyl or $C_1$-$C_3$ alkoxy.

The present invention provides a pyridinylcyanoguanidine derivative of Formula (XXXI), Formula (XXXII), Formula (XXXIII) or Formula (XXXIV), or a pharmaceutically acceptable salt thereof:

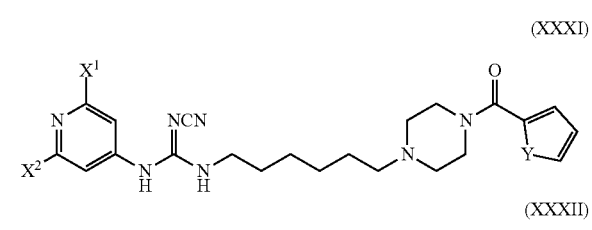
(XXXI)

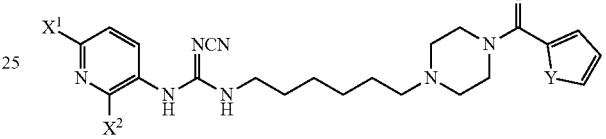
(XXXII)

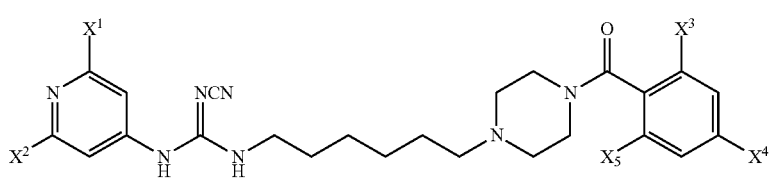
(XXVII)

(XXVIII)

(XXIX)

(XXX)

-continued

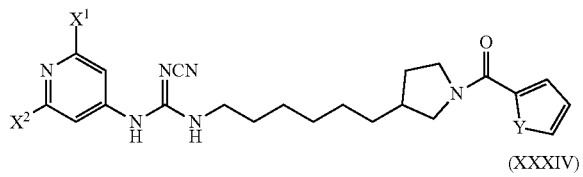
(XXXIII)

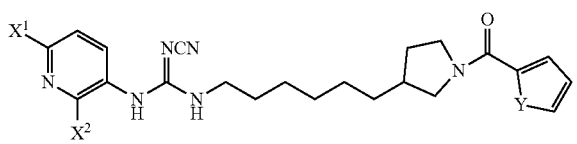
(XXXIV)

where X¹ is hydrogen, fluoro, chloro, bromo, iodo or hydroxyl;
X² is hydrogen, fluoro, chloro, bromo, iodo or hydroxyl; and
Y is a heteroatom, including nitrogen, oxygen, or sulfur.

The present invention provides a pyridinylcyanoguanidine derivative of Formula (XXXV), Formula (XXXVI), Formula (XXXVII) or Formula (XXXVIII), or a pharmaceutically acceptable salt thereof:

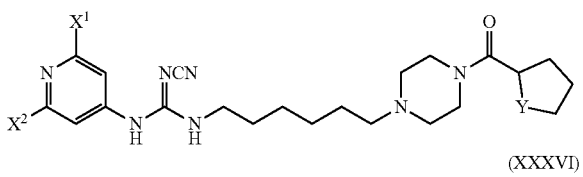
(XXXV)

(XXXVI)

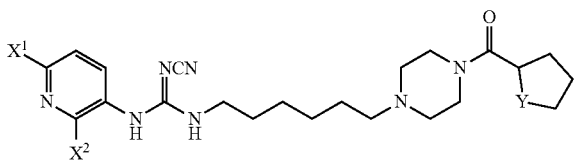
(XXXVII)

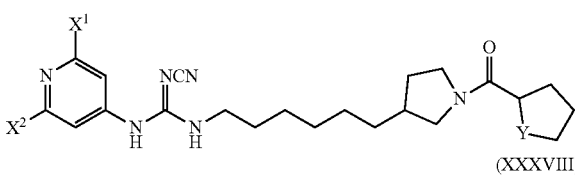
(XXXVIII)

where X¹ is hydrogen, fluoro, chloro, bromo, iodo or hydroxyl;
X² is hydrogen, fluoro, chloro, bromo, iodo or hydroxyl; and
Y is a heteroatom, including nitrogen, oxygen, or sulfur.

In some embodiments, the pyridinylcyanoguanidine derivative or a pharmaceutically acceptable salt thereof is selected from the following pyridinylcyanoguanidine derivatives or pharmaceutically acceptable salts thereof:

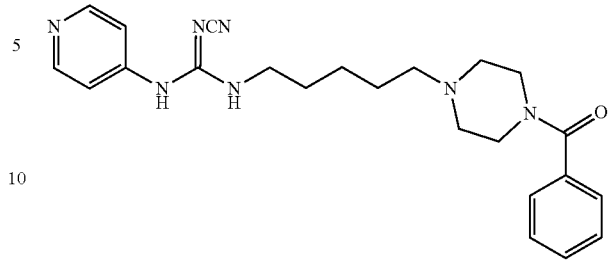
BSS-PC003

BSS-PC004

BSS-PC005

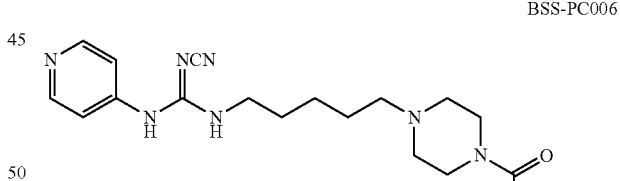
BSS-PC006

BSS-PC007

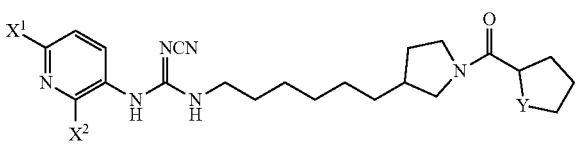

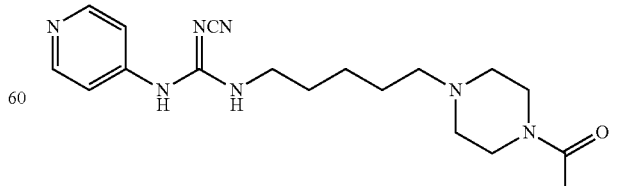

-continued
BSS-PC008
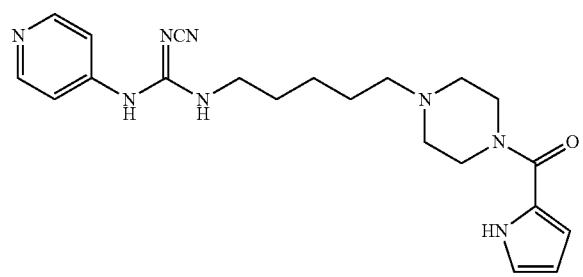
BSS-PC013
BSS-PC009
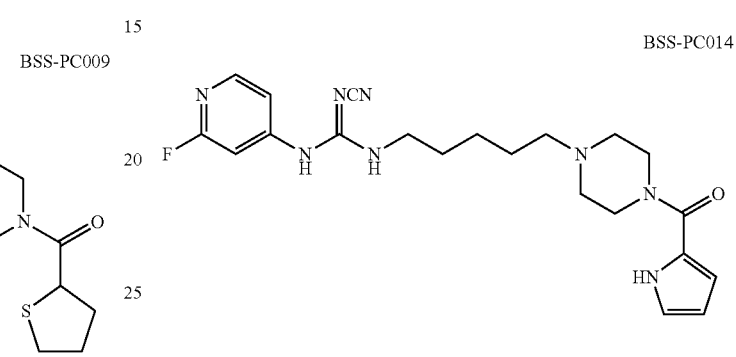
BSS-PC014
BSS-PC0015
BSS-PC010
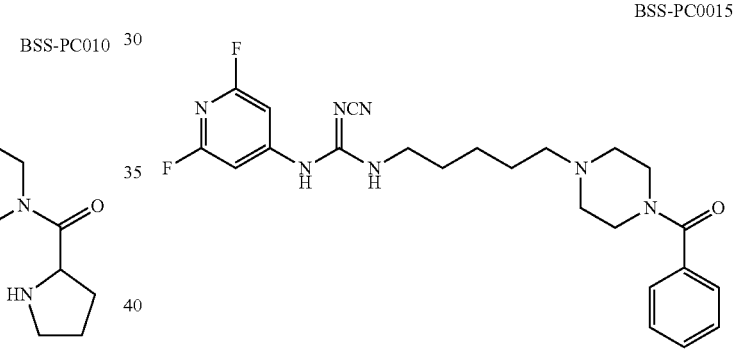
BSS-PC011
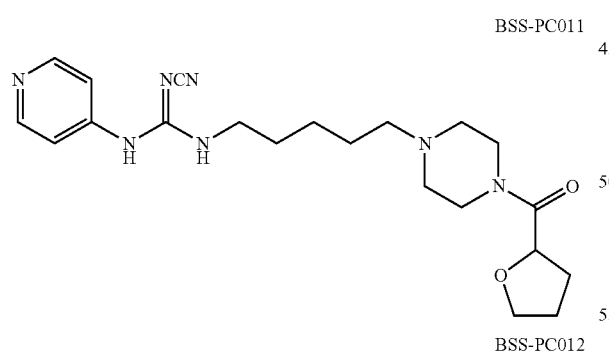
BSS-PC016
BSS-PC012
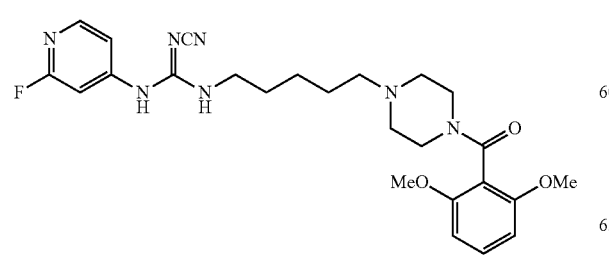
BSS-PC017
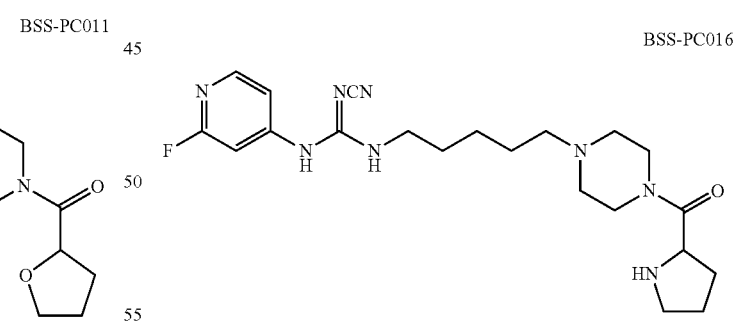
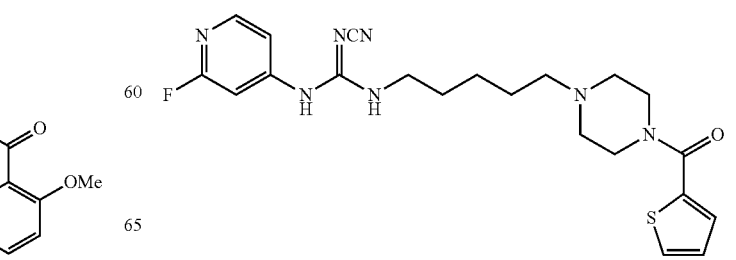

BSS-PC018
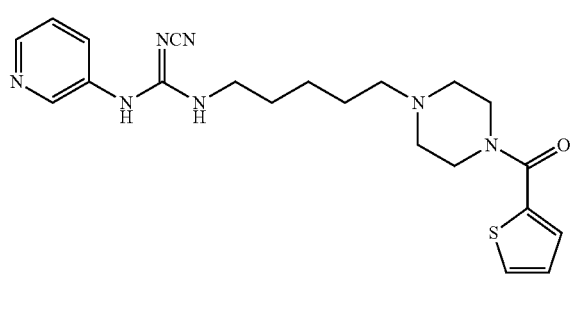
BSS-PC022
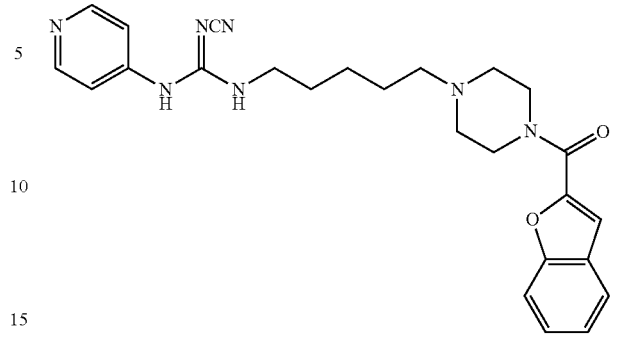
BSS-PC019
BSS-PC023
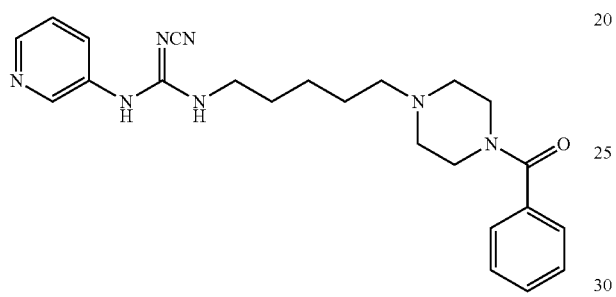
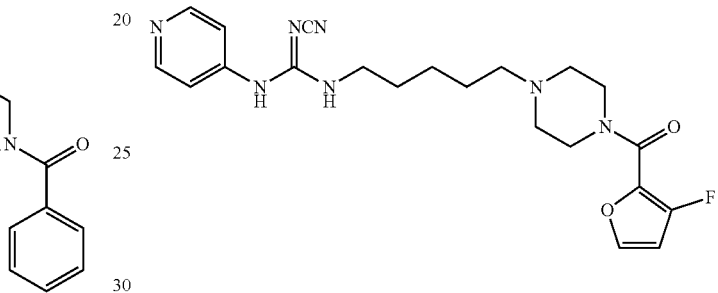
BSS-PC024
BSS-PC020
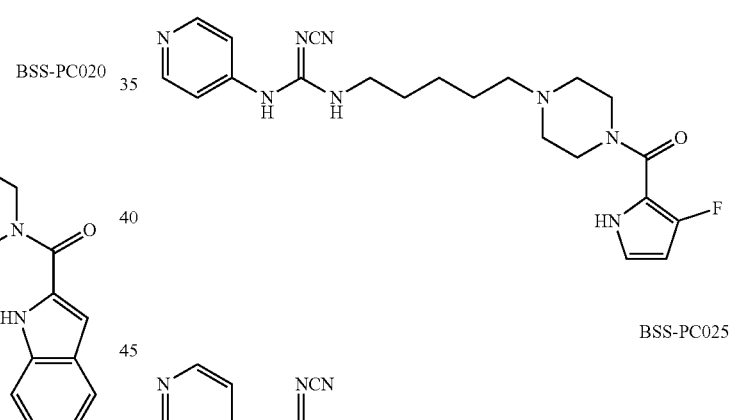
BSS-PC025
BSS-PC021
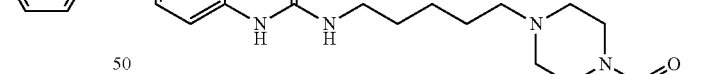
BSS-PC026
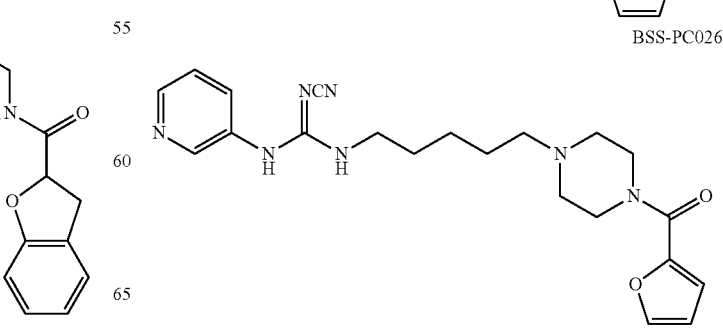

BSS-PC027
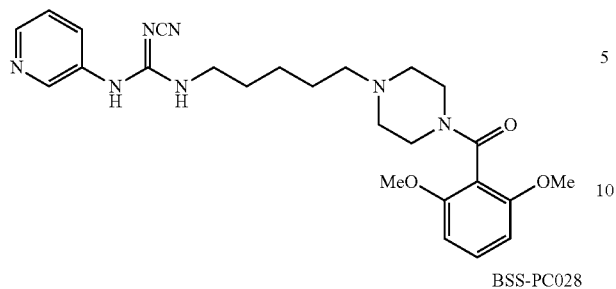
BSS-PC028
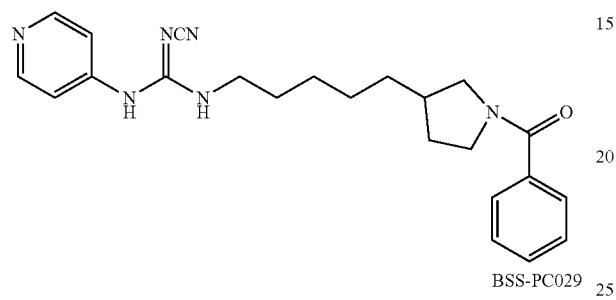
BSS-PC029
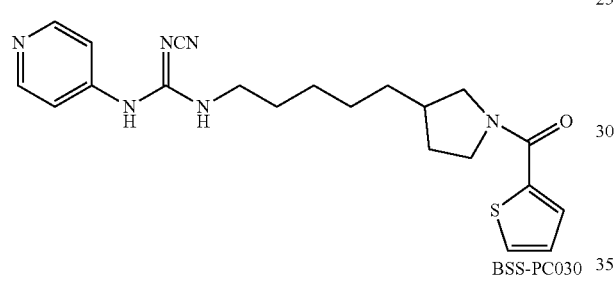
BSS-PC030
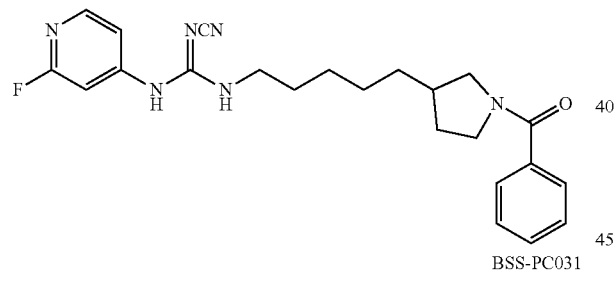
BSS-PC031
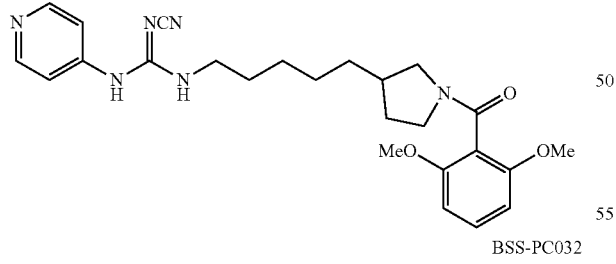
BSS-PC032
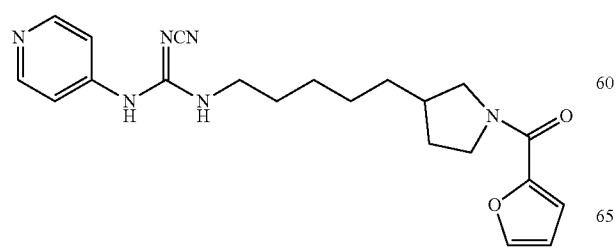
BSS-PC033
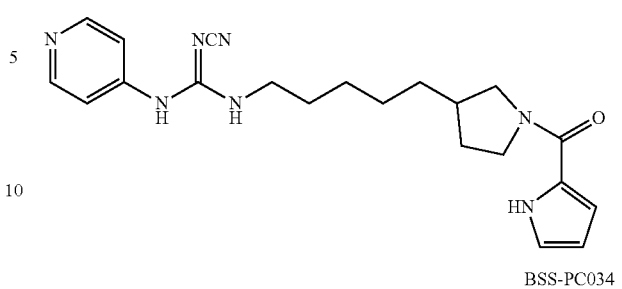
BSS-PC034
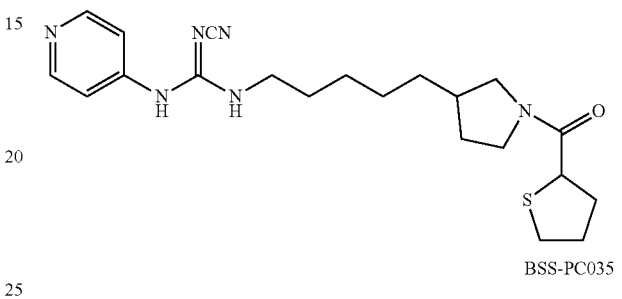
BSS-PC035
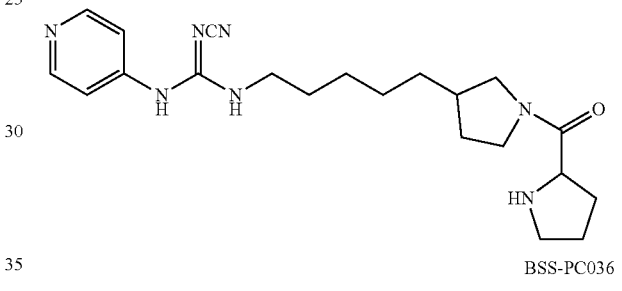
BSS-PC036
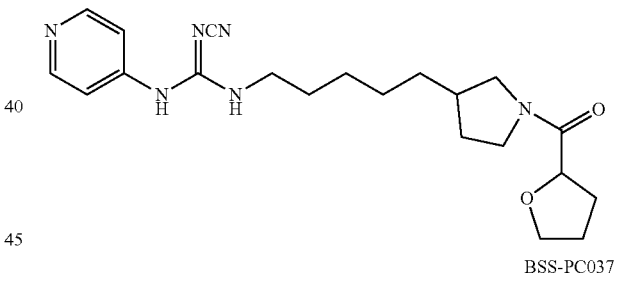
BSS-PC037
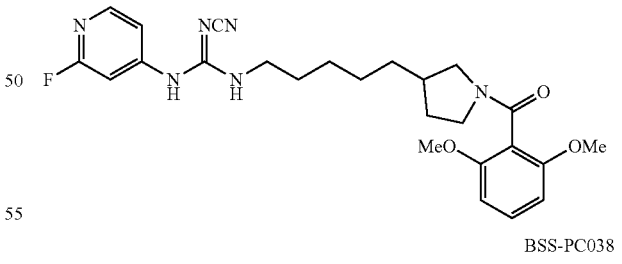
BSS-PC038
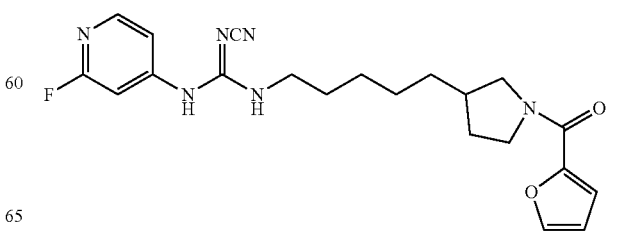

BSS-PC039
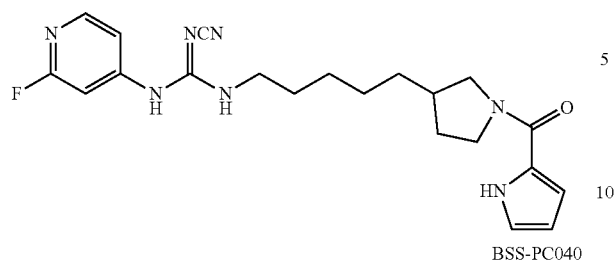
BSS-PC040
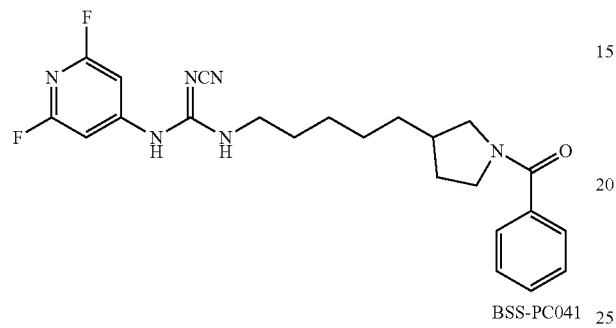
BSS-PC041
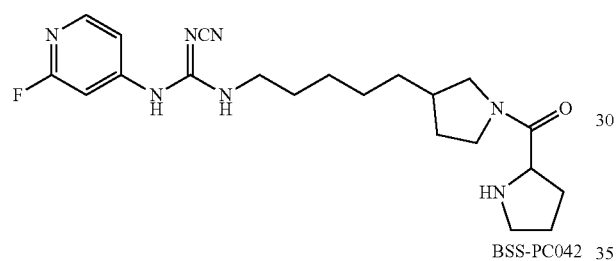
BSS-PC042
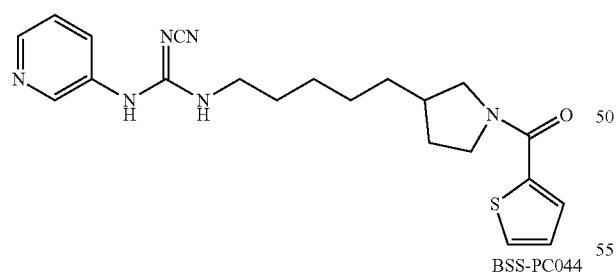
BSS-PC043
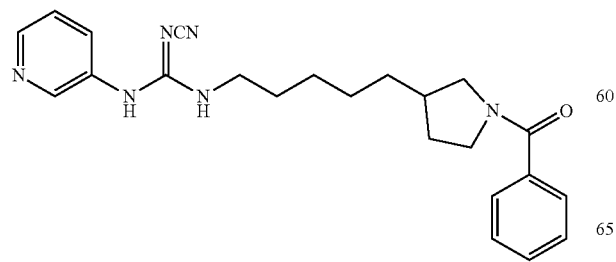
BSS-PC044
BSS-PC045
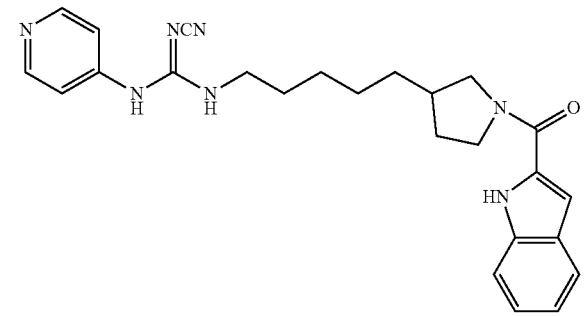
BSS-PC046
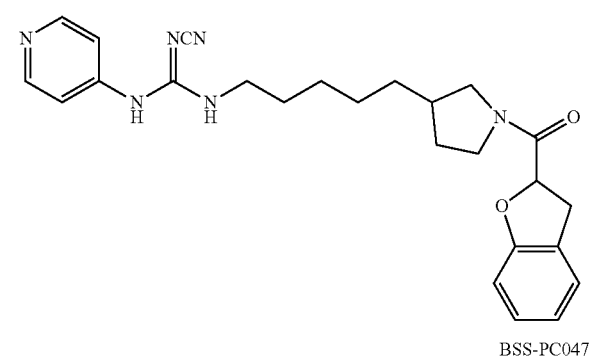
BSS-PC047
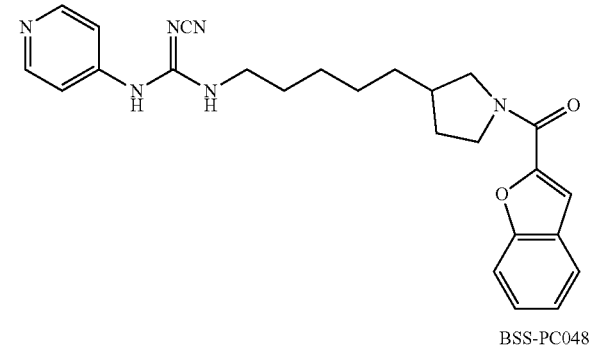
BSS-PC048
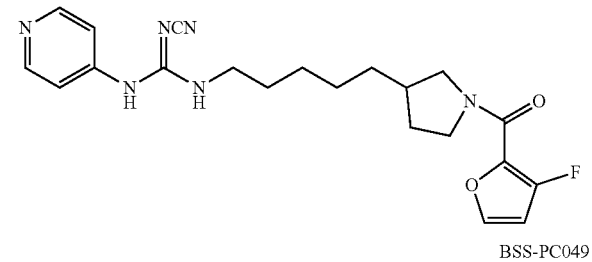
BSS-PC049
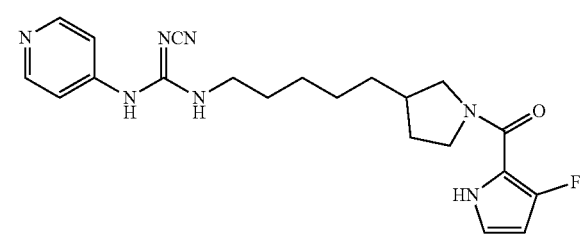

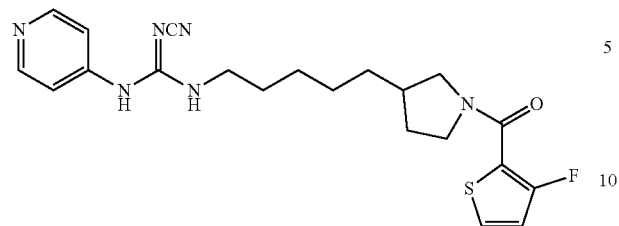
BSS-PC050
BSS-PC051
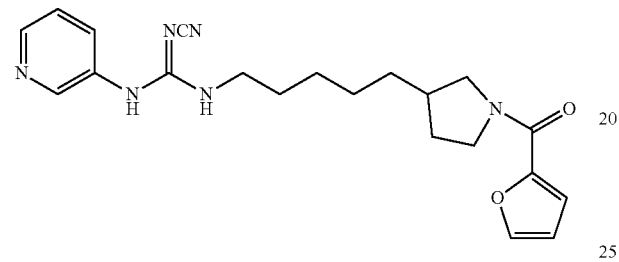
BSS-PC052
BSS-PC053
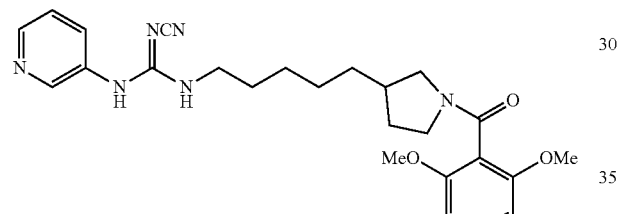
BSS-PC054
BSS-PC055
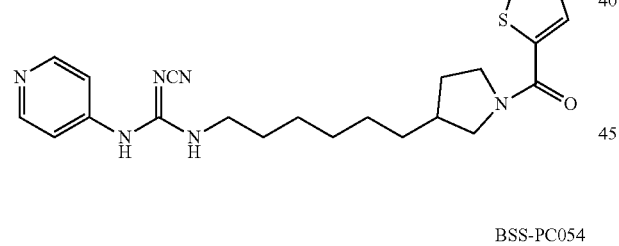
BSS-PC056
BSS-PC057
BSS-PC058
BSS-PC059
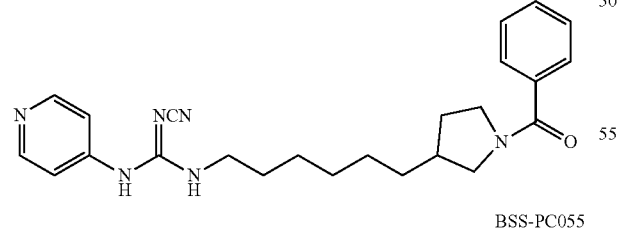
BSS-PC060
BSS-PC061
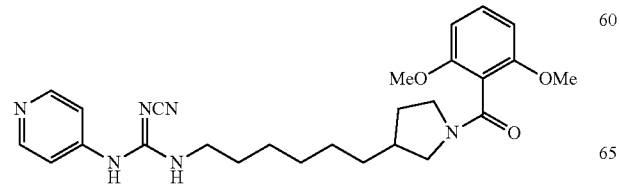
BSS-PC062

-continued
BSS-PC063
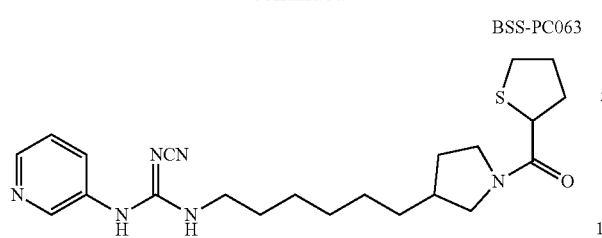
BSS-PC064
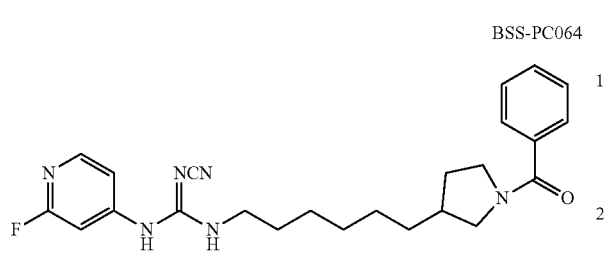
BSS-PC065
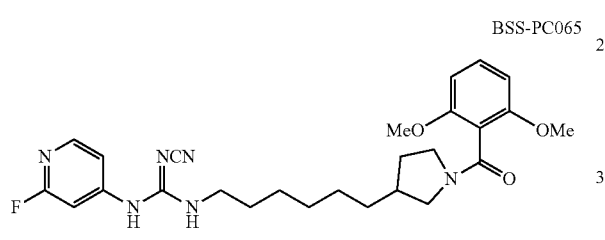
BSS-PC066
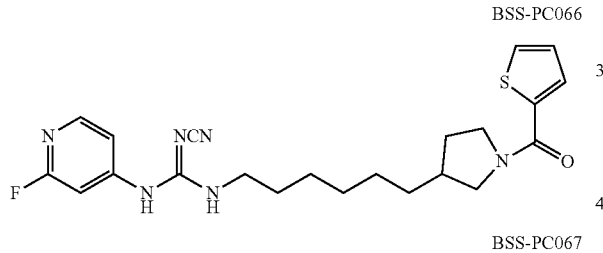
BSS-PC067
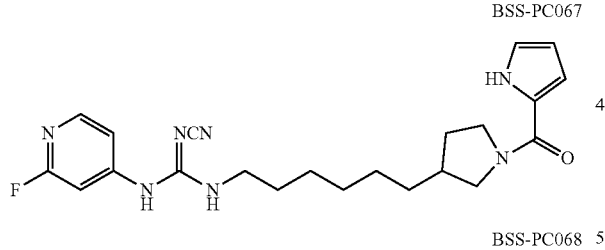
BSS-PC068
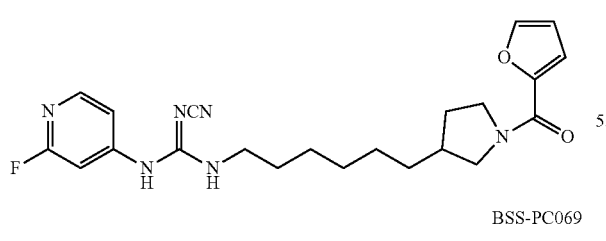
BSS-PC069
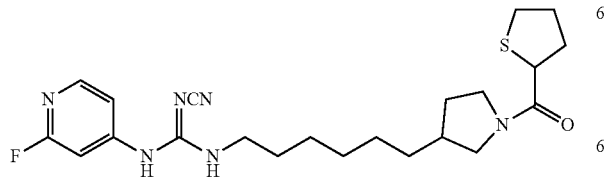
-continued
BSS-PC070
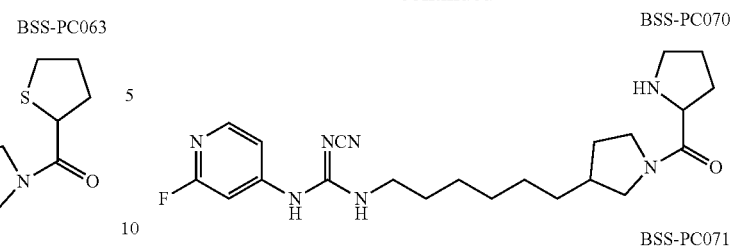
BSS-PC071
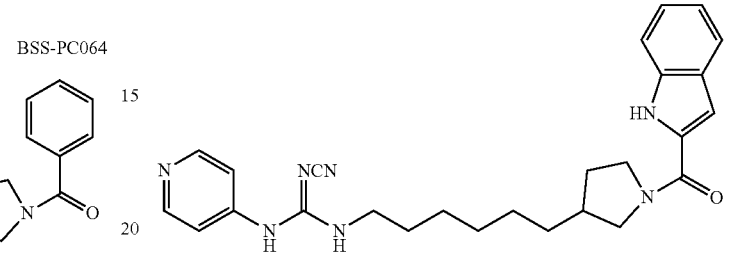
BSS-PC072
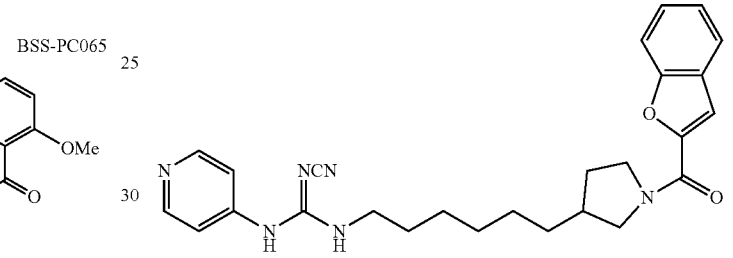
BSS-PC073
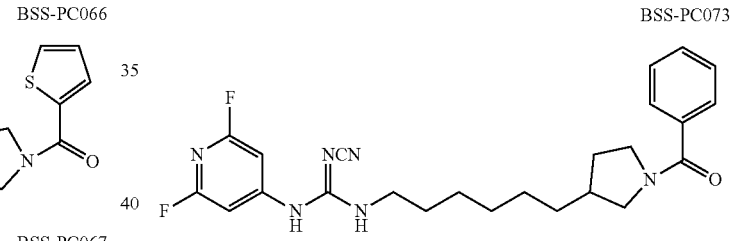
BSS-PC074
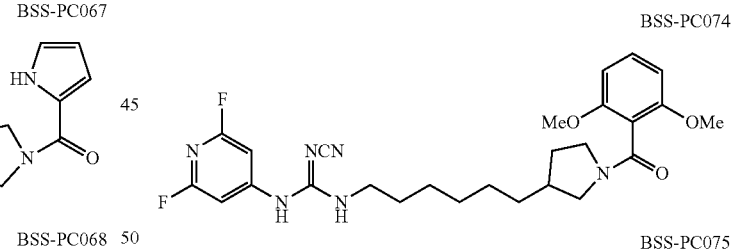
BSS-PC075
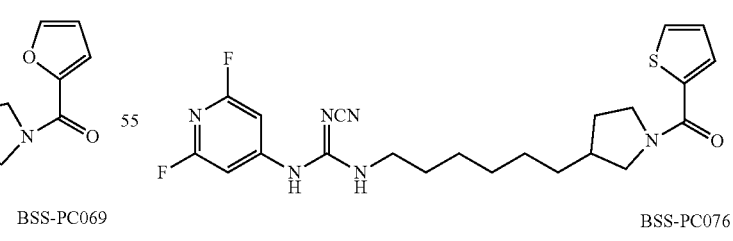
BSS-PC076
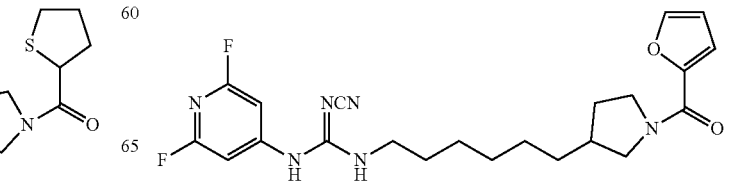

-continued

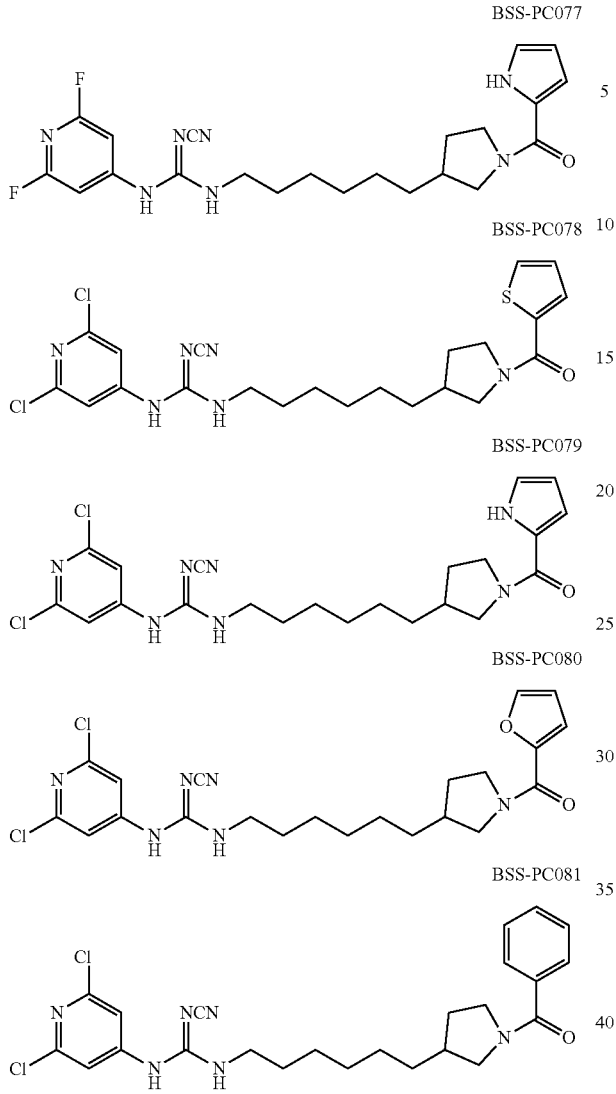

The present invention further provides use of the pyridinylcyanoguanidine derivative or a pharmaceutically acceptable salt thereof in the preparation of drugs for treating diseases associated with abnormal $NAD^+$ expression. The diseases associated with abnormal $NAD^+$ expression includes inflammations, autoimmune diseases, cardiovascular diseases or cancers. The inflammations include osteoarthritis, nephritis or atopic dermatitis; the autoimmune diseases include systemic lupus erythematosus, multiple sclerosis or rheumatoid arthritis; the cardiovascular diseases include atherosclerosis or stroke; and the cancers include breast cancer, prostate cancer, lung cancer, liver cancer, esophageal cancer, gastric cancer, colon cancer, pancreatic cancer or multiple myeloma.

The "pharmaceutically acceptable salt" means a salt that retains the bioavailability and characteristics of the compound of the present invention as a free acid or free base and is obtained by reacting the free acid with a nontoxic inorganic base or organic base or the free base with a nontoxic inorganic acid or organic acid.

The present invention has the following beneficial effects.

The present invention relates to a pyridinylcyanoguanidine derivative or a pharmaceutically acceptable salt thereof, which is useful as an NAMPT inhibitor, and useful as a potential agent for the chemotherapy of a variety of diseases associated with abnormal $NAD^+$ expression. The pyridinylcyanoguanidine derivative has a parent structure including cyanoguanidine attached to piperazine or pyrrolidine by an intermediate aliphatic chain, to which a side arylformyl (or heterocyclylformyl) group and pyridinyl (or substituted pyridinyl) group are attached. This structure comes from the structural optimization of FK866, a high-efficiency NAMPT inhibitor. In the structure, the substituted formyl piperazine and substituted formyl pyrrolidine are the further optimizations on the basis of FK866, which strengthens the interaction with NAMPT. The introduction of cyanoguanidine structure not only further enhances the affinity with NAMPT, but also improves the disadvantage of poor water solubility of FK866, which is more conducive to the subsequent drug test.

FK866 has a structure shown below:

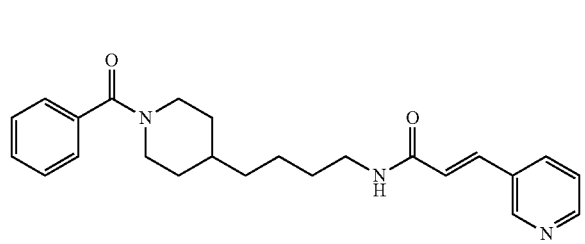 [SMILES: O=C(/C=C/c1cccnc1)NCCCCC1CCN(C(=O)c2ccccc2)CC1]

DETAILED DESCRIPTION

The present invention will be further explained below by way of examples. The following examples are merely used to illustrate the present invention, but not intended to limit the scope of the present invention.

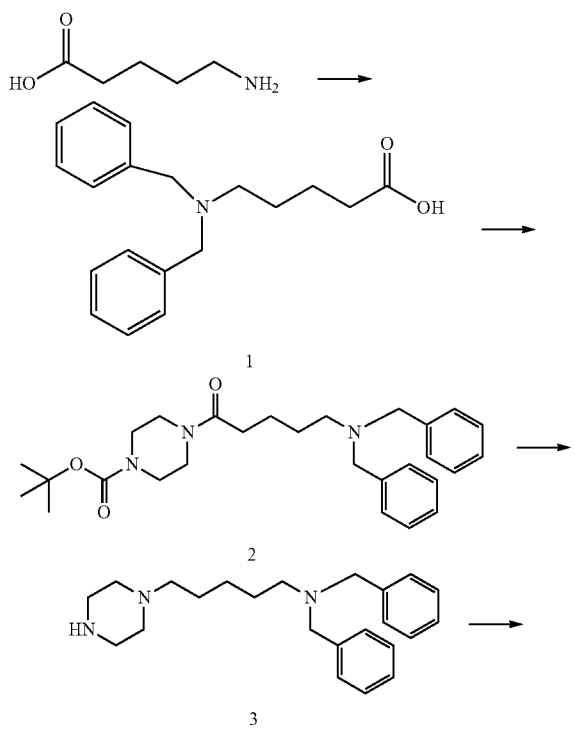

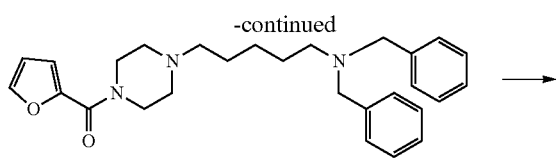

4

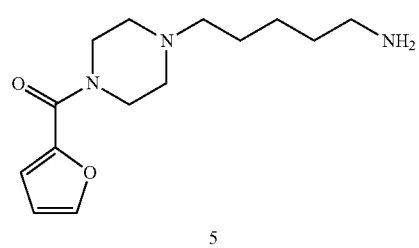

5

Example 1

11.7 g of 5-aminopentanoic acid was added to 130 ml of dichloroethane, 26.5 g of benzaldehyde, and then 13.3 g of triethyl amine were added, heated to reflux for 2 hrs, and then cooled to room temperature. 15.75 g of sodium cyanoborohydride was added, and refluxed overnight. The reaction solution was concentrated under reduced pressure, separated by column chromatography (dichloromethane:methanol 10:1 vol/vol), to obtain 11.3 g of sticky N,N-dibenzyl-5-aminopentanoic acid (1), $^1$HNMR (400 MHz, CDCl3): δ=7.45-7.26 (m, 10H), 4.71 (s, 4H), 3.43-3.35 (m, 2H), 2.41-2.30 (m, 2H), 2.11-1.95 (m, 2H), 1.27-1.19 (m, 2H); [M+H]: 298.3.

Example 2

2.97 g of N,N-dibenzyl-5-aminopentanoic acid (1) was dissolved in dichloromethane, and 1.4 g of N,N'-carbonyldiimidazole (CDI) was added in batches. After stirring at room temperature for half an hour, a solution of 1.863 g of Boc-piperazine dissolved in 10 ml of dichloromethane was added dropwise, and stirred overnight. The reaction solution was concentrated under reduced pressure, and separated by column chromatography (ethyl acetate: petroleum ether 3:1 vol/vol), to obtain 3.1 g of a sticky product (2). $^1$HNMR (400 MHz, CDCl3): δ=7.49-7.24 (m, 10H), 3.55 (s, 4H), 3.49-3.25 (m, 8H), 2.49-2.39 (m, 2H), 2.21-2.15 (m, 2H), 1.78-1.54 (m, 4H), 1.50 (s, 9H); [M+H]: 466.6.

Example 3

3 g of the compound (2) obtained in the previous step was dissolved in 30 ml of tetrahydrofuran, and cooled to 0° C. 2.5 g of lithium aluminum hydride was added in batches, heated to room temperature and stirred for 3 hrs. 10 ml of a 50 wt % sodium hydroxide solution was added, and then 30 ml of dichloromethane was added. The organic layer was separated, washed with water, dried over anhydrous sodium sulfate, concentrated under reduced pressure, and separated by column chromatography (dichloromethane:methanol: aqueous ammonia 20:1:0.01 vol/vol/vol), to obtain 2.12 g of a yellow sticky product (3). $^1$HNMR (400 MHz, CDCl3): δ=7.45-7.21 (m, 10H), 3.56 (s, 4H), 3.48-3.39 (m, 2H), 2.49-2.35 (m, 4H), 2.34-2.30 (m, 2H), 2.29-2.26 (m, 4H), 1.61-1.55 (m, 2H), 1.41-1.35 (m, 2H), 1.34-1.25 (m, 2H); [M+H]: 352.5.

Example 4

2 g of the compound (3) obtained in the previous step was dissolved in 20 ml of dichloromethane, and then 1.8 g of triethylamine was added and cooled to 0° C. 1.58 g of furoyl chloride was added dropwise, heated to room temperature and stirred overnight. The reaction solution was concentrated under reduced pressure, and separated by column chromatography (ethyl acetate:petroleum ether 5:1 vol/vol), to obtain 2.12 g of a sticky product (4). $^1$HNMR (400 MHz, CDCl3): δ=7.50-7.47 (d, 1H), 7.38-7.20 (m, 10H), 7.09-7.07 (d, 1H), 6.47-6.44 (m, 1H), 3.70 (s, 4H), 3.17-3.11 (m, 4H), 2.91-2.80 (m, 2H), 2.63-2.55 (m, 2H), 2.52-2.48 (m, 2H), 2.60-2.46 (m, 4H), 1.52-1.36 (m, 4H); [M+H]: 446.6.

Example 5

2 g of the compound (4) obtained in the previous step was dissolved in 20 ml of methanol, and then 0.2 g of Pd/C (5%) was added. After reaction at room temperature under 4 atm for 10 hrs, the reaction solution was filtered. The filtrate was concentrated under reduced pressure to obtain 1.2 g of the product 1-furoyl-4-(5'-amino-1'-pentyl)piperazine (5) MS (m/z), 266 (M+1). The product was directly used in the next step.

The following compounds can be prepared according to the above method of preparing the compound 5 starting from 5-aminopentanoic acid:

| Preparation number | Name of Compound | Structure | MS (m/z) |
|---|---|---|---|
| 6 | 1-benzoyl-4-(5'-amino-1'-pentyl)piperazine | 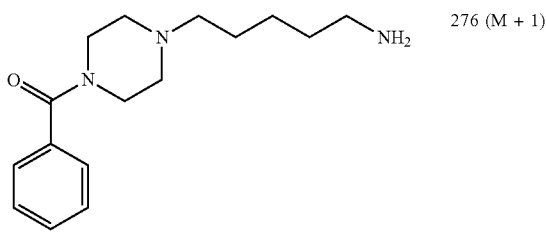 | 276 (M + 1) |

-continued

| Preparation number | Name of Compound | Structure | MS (m/z) |
|---|---|---|---|
| 7 | 1-(2,6-dimethoxybenzoyl)-4-(5'-amino-1'-pentyl)piperazine | 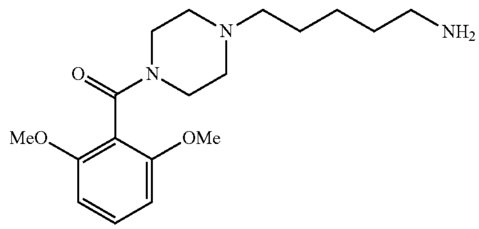 [SMILES: COc1cccc(OC)c1C(=O)N1CCN(CCCCCN)CC1] | 336 (M + 1) |
| 8 | 1-(2-thienylformyl)-4-(5'-amino-1'-pentyl)piperazine | 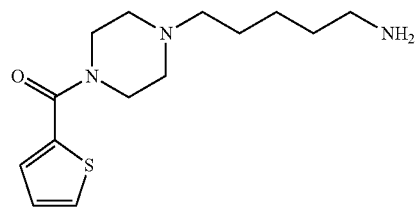 [SMILES: NCCCCCN1CCN(C(=O)c2cccs2)CC1] | 282 (M + 1) |
| 8-1 | 1-(2-tetrahydrothienylformyl)-4-(5'-amino-1'-pentyl)piperazine | 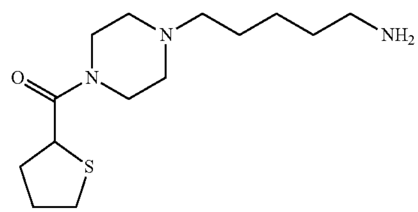 [SMILES: NCCCCCN1CCN(C(=O)C2CCCS2)CC1] | 286 (M + 1) |
| 8-2 | 1-(2-tetrahydrofurylfuryl)-4-(5'-amino-1'-pentyl)piperazine | 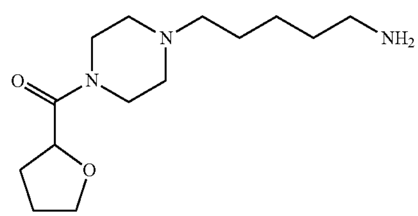 [SMILES: NCCCCCN1CCN(C(=O)C2CCCO2)CC1] | 270 (M + 1) |
| 8-3 | 1-(2-pyrrolylformyl)-4-(5'-amino-1'-pentyl)piperazine | 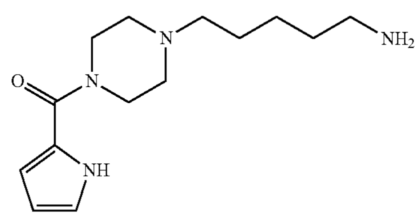 [SMILES: NCCCCCN1CCN(C(=O)c2ccc[nH]2)CC1] | 265 (M + 1) |
| 8-4 | 1-(2-pyrrolidinylformyl)-4-(5'-amino-1'-pentyl)piperazine | 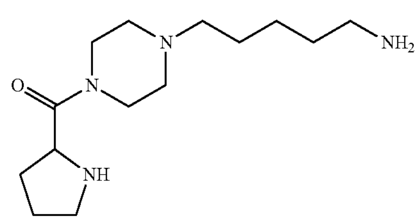 [SMILES: NCCCCCN1CCN(C(=O)C2CCCN2)CC1] | 269 (M + 1) |
| 8-5 | 1-(3-fluoro-2-furylformyl)-4-(5'-amino-1'-pentyl)piperazine | 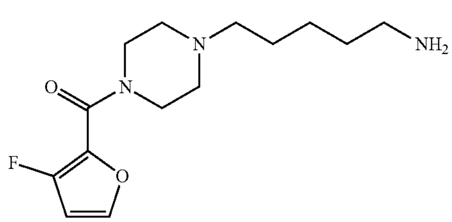 [SMILES: NCCCCCN1CCN(C(=O)c2occc2F)CC1] | 284 (M + 1) |

-continued
| Preparation number | Name of Compound | Structure | MS (m/z) |
|---|---|---|---|
| 8-6 | 1-(3-fluoro-2-pyrrolylformyl)-4-(5'-amino-1'-pentyl)piperazine | 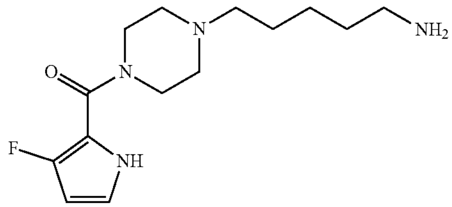 [SMILES: NCCCCCN1CCN(C(=O)c2[nH]ccc2F)CC1] | 283 (M + 1) |
| 8-7 | 1-(3-fluoro-2-thienylformyl)-4-(5'-amino-1'-pentyl)piperazine | 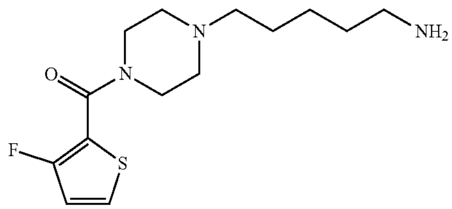 [SMILES: NCCCCCN1CCN(C(=O)c2sccc2F)CC1] | 300 (M + 1) |
| 9 | 1-(2-indolylformyl)-4-(5'-amino-1'-pentyl)piperazine | 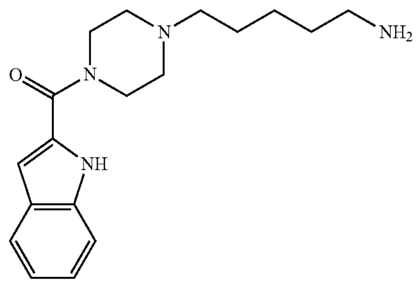 [SMILES: NCCCCCN1CCN(C(=O)c2cc3ccccc3[nH]2)CC1] | 315 (M + 1) |
| 9-1 | 1-(2-benzofurylformyl)-4-(5'-amino-1'-pentyl)piperazine | 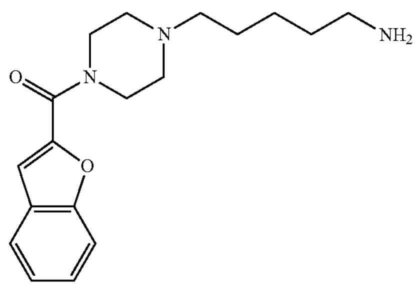 [SMILES: NCCCCCN1CCN(C(=O)c2cc3ccccc3o2)CC1] | 316 (M + 1) |
| 9-2 | 1-(2-benzotetrahydrofurylfuryl)-4-(5'-amino-1'-pentyl)piperazine | 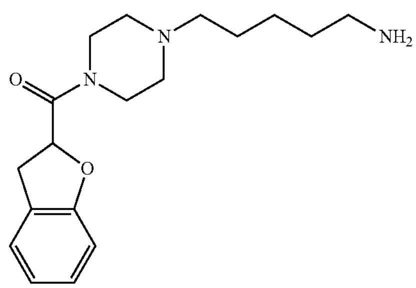 [SMILES: NCCCCCN1CCN(C(=O)C2Cc3ccccc3O2)CC1] | 318 (M + 1) |
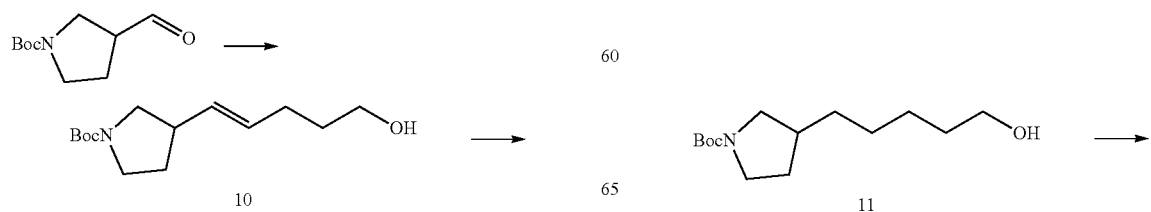

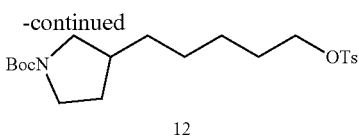

12

Example 6

2.1 g of triphenylphosphine was dissolved in 20 ml of tetrahydrofuran, and then 2.5 g of 4-bromo-1-butanol was added and refluxed overnight under a nitrogen atmosphere. A large amount of solid was precipitated, which was allowed to stand still. The liquid was poured out, and then the white solid was washed twice with 10 ml of anhydrous tetrahydrofuran. 20 ml of anhydrous tetrahydrofuran was added, and cooled to −10° C. 5.6 ml of a n-butyl lithium solution (2.5 M) was slowly added under a nitrogen atmosphere, during which the temperature was controlled at −5° C. or below. After that, the reaction was continued at this temperature with stirring for further 2 hrs, and then cooled to −10° C. or below. A solution of 2 g of 1-Boc-3-pyrrolidinylcarboxaldehyde dissolved in 20 ml of anhydrous tetrahydrofuran was added dropwise to the above reaction solution. The reaction was continued at this temperature for 2 hrs, heated to room temperature and stirred overnight. The reaction solution was cooled to 0° C., 10 ml of a saturated ammonium chloride solution was added dropwise, and 20 ml of water was added. The organic layer was separated, and the aqueous layer was extracted twice with 30 ml of ethyl acetate. The organic layers were combined, and washed sequentially with a saturate sodium chloride solution and water. The organic layer was dried over anhydrous magnesium sulfate, concentrated under reduced pressure, and separated by column chromatography (EA/PE vol/vol=1:10-1:1, gradient elution, where EA is ethyl acetate, and PE is petroleum ether) to obtain 2.3 g of an oily product 1-Boc-3-(5'-hydroxy-1'-en-pentyl)pyrrolidine (10).

Example 7

0.5 g of 1-Boc-3-(5'-hydroxy-1'-en-pentyl)pyrrolidine (10) was dissolved in 10 ml of methanol, and then 0.025 g of Pd/C (5%) was added and heated to 40° C. The reaction was continued under a hydrogen atmosphere (4 atm) for 48 hrs, and then the reaction solution was filtered. The filtrate was concentrated under reduce pressure, and separated by column chromatography (EA/PE vol/vol=1:1-10:1, gradient elution) to obtain 0.45 g of an oily product 1-Boc-3-(5'-hydroxy-1'-pentyl)pyrrolidine (11).

Example 8

0.45 g of 1-Boc-3-(5'-hydroxy-1'-pentyl)pyrrolidine (11) was dissolved in 10 ml of dichloromethane, and then cooled to 0° C. 1.5 ml of triethyl amine was added. Then the solution was added dropwise to a solution of 1.2 g of p-toluenesulfonyl chloride dissolved in 6 ml of dichloromethane under a nitrogen atmosphere, and reacted overnight with stirring. A saturated ammonium chloride solution was added. The organic layer was separated, and then the aqueous layer was extracted with 10 ml of dichloromethane. The organic layers were combined, dried over anhydrous sodium sulfate, and filtered. The filtrate was concentrated under reduce pressure, and separated by column chromatography (EA/PE vol/vol=1:4), to obtain 0.51 g of an oily product 1-Boc-3-(5'-p-toluenesulfonyl-1'-pentyl)pyrrolidine (12).

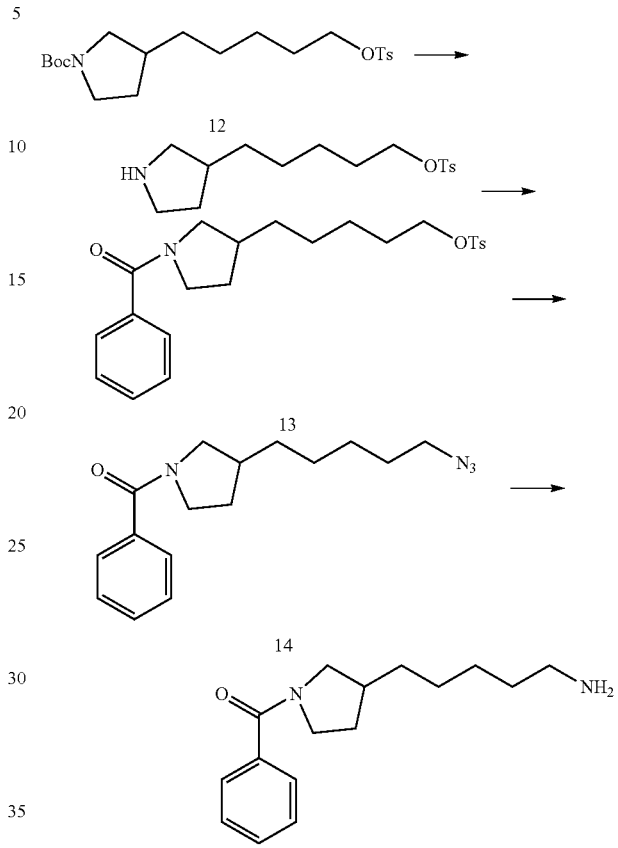

Example 9

0.5 g of 1-Boc-3-(5'-p-toluenesulfonyl-1'-pentyl)pyrrolidine (12) was dissolved in 10 ml of dichloromethane, and then 2 ml of trifluoroacetic acid was added, stirred overnight at room temperature and concentrated under reduced pressure. 10 ml of dichloromethane was added, and then 1 ml of triethyl amine was added dropwise and cooled to 0° C. Under a nitrogen atmosphere, 1.2 g of benzoyl chloride was added, and reacted overnight with stirring. A saturated ammonium chloride solution was added. The organic layer was separated, and then the aqueous layer was extracted with 10 ml of dichloromethane. The organic layers were combined, dried over anhydrous sodium sulfate, and filtered. The filtrate was concentrated under reduce pressure, and separated by column chromatography (EA/PE vol/vol=1:2-2:1, gradient elution), to obtain 0.43 g of an oily product 1-benzoyl-3-(5'-p-toluenesulfonyl-1'-pentyl)pyrrolidine (13).

Example 10

0.39 g of 1-benzoyl-3-(5'-p-toluenesulfonyl-1'-pentyl)pyrrolidine (13) was dissolved in 4 ml of N,N-dimethyl formamide (DMF), and then 0.15 g of sodium azide was added, heated to 70° C. and reacted overnight. After concentration under reduced pressure, 10 ml of dichloromethane was added, and washed sequentially with water and a saturated sodium chloride solution. The reaction solution was concentrated under reduced pressure, and separated by column chromatography (EA/PE vol/vol=1:4-1:1, gradient elution), to obtain 0.24 g of an oily product 1-benzoyl-3-(5'-azido-1'-pentyl)pyrrolidine (14).

Example 11

0.18 of 1-benzoyl-3-(5'-azido-1'-pentyl)pyrrolidine (14) was dissolved in 5 ml of tetrahydrofuran, and then 0.15 g of triphenylphosphine and 2 drops of water were added and refluxed overnight. After concentration under reduced pressure, 10 ml of dichloromethane was added, and washed sequentially with water and a saturated sodium chloride solution. The reaction solution was concentrated under reduced pressure, and separated by column chromatography (dichloromethane/methanol/aqueous ammonia=10:1:0.1 vol/vol/vol), to obtain 0.16 g of an oily product 1-benzoyl-3-(5'-amino-1'-pentyl)pyrrolidine (15). LCMS: 261[M+H].

The following compounds can be prepared according to the above method of preparing the compound 15 starting from the compound 12:

| Preparation number | Name of Compound | Structure | MS (m/z) |
|---|---|---|---|
| 16 | 1-(2,6-dimethoxybenzoyl)-3-(5'-amino-1'-pentyl)pyrrolidine | 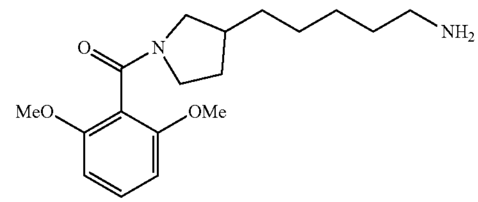 [SMILES: COc1cccc(OC)c1C(=O)N1CCC(CCCCCN)C1] | 321 (M + 1) |
| 17 | 1-(2,6-dimethoxybenzoyl)-3-(6'-amino-1'-hexyl)pyrrolidine | 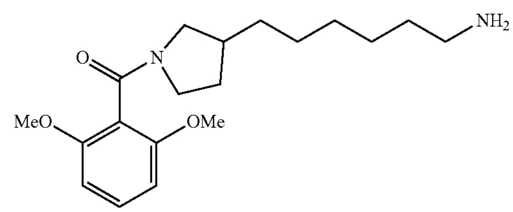 [SMILES: COc1cccc(OC)c1C(=O)N1CCC(CCCCCCN)C1] | 335 (M + 1) |
| 18 | 1-benzoyl-3-(6'-amino-1'-hexyl)pyrrolidine | 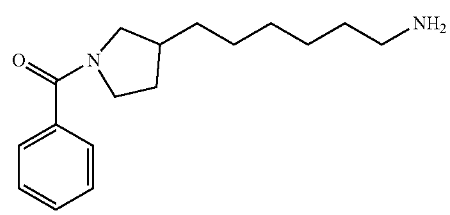 [SMILES: NCCCCCCC1CCN(C(=O)c2ccccc2)C1] | 275 (M + 1) |
| 19 | 1-furoyl-3-(5'-amino-1'-pentyl)pyrrolidine | 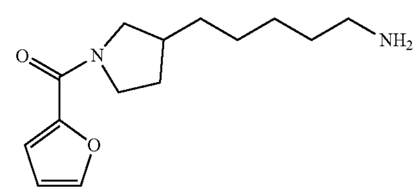 [SMILES: NCCCCCC1CCN(C(=O)c2ccco2)C1] | 251 (M + 1) |
| 19-1 | 1-furoyl-3-(6'-amino-1'-hexyl)pyrrolidine | 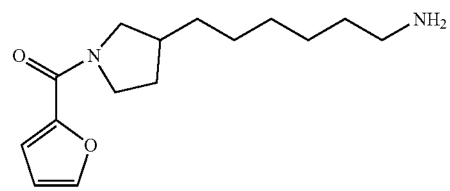 [SMILES: NCCCCCCC1CCN(C(=O)c2ccco2)C1] | 265 (M + 1) |
| 20 | 1-(2-thienylformyl)-3-(5'-amino-1'-pentyl)pyrrolidine | 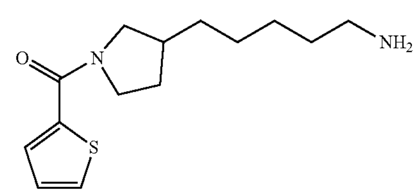 [SMILES: NCCCCCC1CCN(C(=O)c2cccs2)C1] | 267 (M + 1) |

-continued

| Preparation number | Name of Compound | Structure | MS (m/z) |
|---|---|---|---|
| 20-1 | 1-(2-thienylformyl)-3-(6'-amino-1'-hexyl)pyrrolidine | 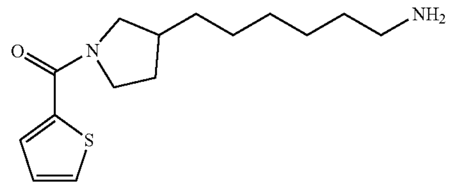 [SMILES: NCCCCCCC1CCN(C(=O)c2cccs2)C1] | 281 (M + 1) |
| 21 | 1-(2-pyrrolylformyl)-3-(5'-amino-1'-pentyl)pyrrolidine | 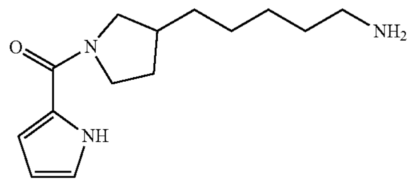 [SMILES: NCCCCCC1CCN(C(=O)c2ccc[nH]2)C1] | 250 (M + 1) |
| 22 | 1-(2-pyrrolylformyl)-3-(6'-amino-1'-hexyl)pyrrolidine | 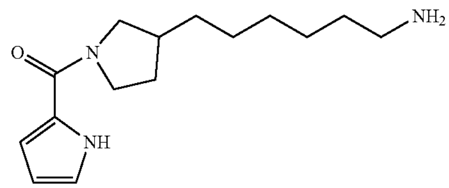 [SMILES: NCCCCCCC1CCN(C(=O)c2ccc[nH]2)C1] | 264 (M + 1) |
| 23 | 1-(2-pyrrolidinylformyl)-3-(5'-amino-1'-pentyl)pyrrolidine | 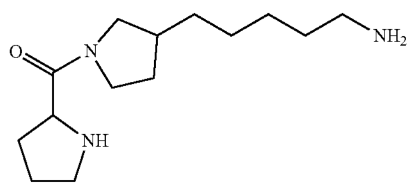 [SMILES: NCCCCCC1CCN(C(=O)C2CCCN2)C1] | 254 (M + 1) |
| 23-1 | 1-(2-pyrrolidinylformyl)-3-(6'-amino-1'-hexyl)pyrrolidine | 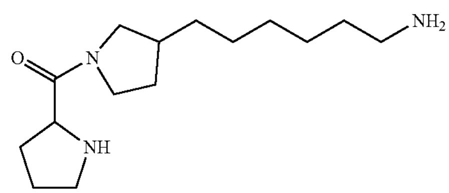 [SMILES: NCCCCCCC1CCN(C(=O)C2CCCN2)C1] | 268 (M + 1) |
| 24 | 1-(2-tetrahydrofurylfuryl)-3-(5'-amino-1'-pentyl)pyrrolidine | 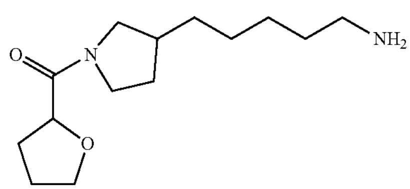 [SMILES: NCCCCCC1CCN(C(=O)C2CCCO2)C1] | 255 (M + 1) |
| 25 | 1-(2-tetrahydrothienylformyl)-3-(5'-amino-1'-pentyl)pyrrolidine | 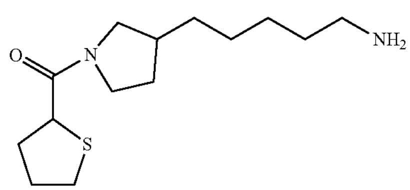 | 271 (M + 1) |
| 25-1 | 1-(2-tetrahydrothienylformyl)-3-(6'-amino-1'-hexyl)pyrrolidine | 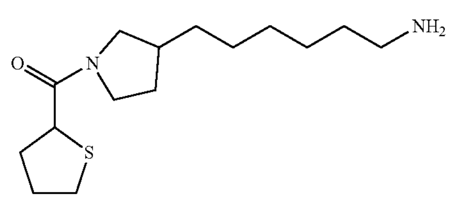 [SMILES: NCCCCCCC1CCN(C(=O)C2CCCS2)C1] | 285 (M + 1) |

| Preparation number | Name of Compound | Structure | MS (m/z) |
|---|---|---|---|
| 25-2 | 1-(3-fluoro-2-thienylformyl)-3-(5'-amino-1'-pentyl)pyrrolidine | 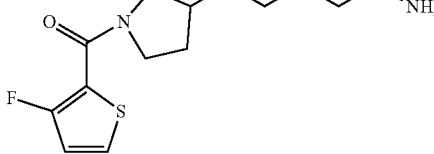 | 285 (M + 1) |
| 25-3 | 1-(3-fluoro-2-pyrrolylformyl)-3-(5'-amino-1'-pentyl)pyrrolidine | 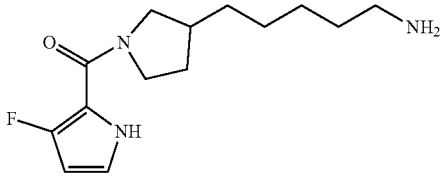 [SMILES: NCCCCCC1CCN(C(=O)c2[nH]ccc2F)C1] | 268 (M + 1) |
| 25-4 | 1-(3-fluoro-2-furylformyl)-3-(5'-amino-1'-pentyl)pyrrolidine | 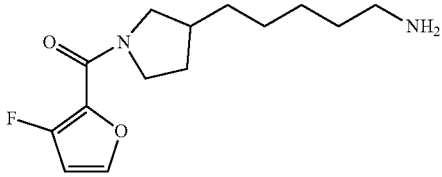 [SMILES: NCCCCCC1CCN(C(=O)c2occc2F)C1] | 269 (M + 1) |
| 26 | 1-(2-indolylformyl)-3-(5'-amino-1'-pentyl)pyrrolidine | 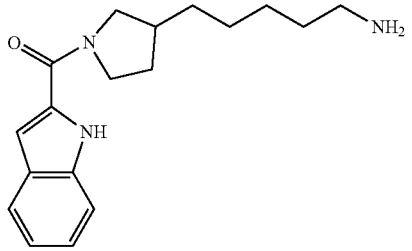 [SMILES: NCCCCCC1CCN(C(=O)c2cc3ccccc3[nH]2)C1] | 300 (M + 1) |
| 26-1 | 1-(2-indolylformyl)-3-(6'-amino-1'-hexyl)pyrrolidine | 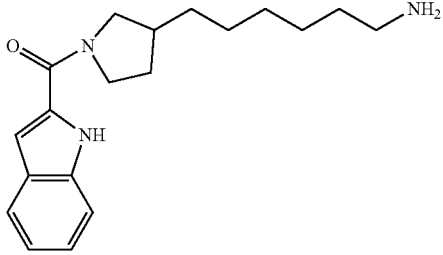 [SMILES: NCCCCCCC1CCN(C(=O)c2cc3ccccc3[nH]2)C1] | 314 (M + 1) |
| 27 | 1-(2-benzofurylformyl)-3-(5'-amino-1'-pentyl)pyrrolidine | 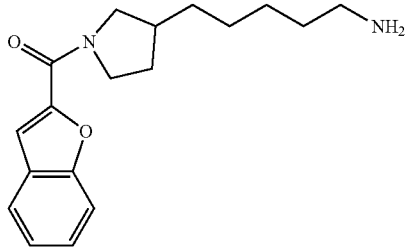 [SMILES: NCCCCCC1CCN(C(=O)c2cc3ccccc3o2)C1] | 301 (M + 1) |

-continued

| Preparation number | Name of Compound | Structure | MS (m/z) |
|---|---|---|---|
| 27-1 | 1-(2-benzofurylformyl)-3-(6'-amino-1'-hexyl)pyrrolidine | 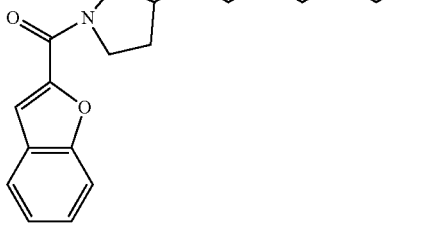 | 315 (M + 1) |
| 27-2 | 1-(2-benzyltetrahydrofurylfuryl)-3-(5'-amino-1'-pentyl)pyrrolidine | 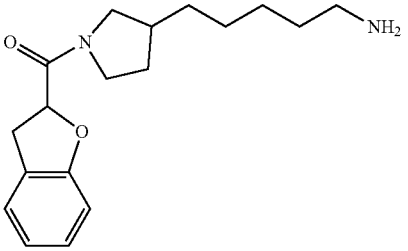 [SMILES: NCCCCCC1CCN(C(=O)C2Cc3ccccc3O2)C1] | 303 (M + 1) |

Example 12

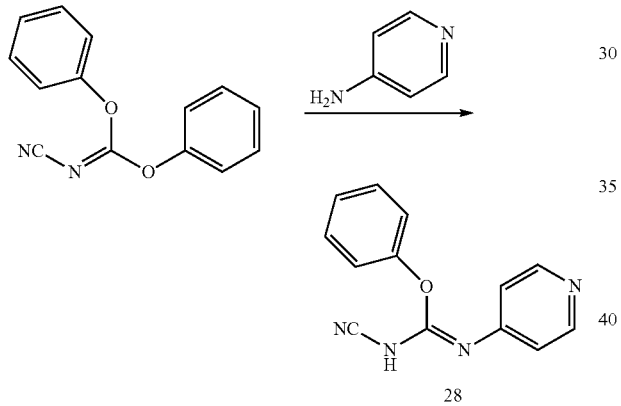

A solution of 4-aminopyridine (0.612 g), diphenyl N-cyanocarbonimidate (1.540 g) and triethylamine (1.0 mL) in acetonitrile (15 ml) was stirred at 80° C. for 2 hrs, and then at room temperature for 12 hrs. The reaction mixture was concentrated under reduced pressure, to obtain a residue. The residue was diluted with ethyl acetate (20 ml), and washed twice with water (20 ml). The organic layer was dried over anhydrous sodium sulfate, and concentrated under reduced pressure to obtain a solid. The solid was washed by stirring in isopropanol (5 ml), filtered and dried to obtain 1.2 g of 1-cyano-2-phenyl-3-(pyridin-4-yl)isourea (28) as a solid. LCMS: 239.10[M+H].

The following compounds can be prepared according to the method in Example 12:

| Preparation number | Name of Compound | Structure | MS (m/z) |
|---|---|---|---|
| 29 | 1-cyano-2-phenyl-3-(pyridin-3-yl)isourea | 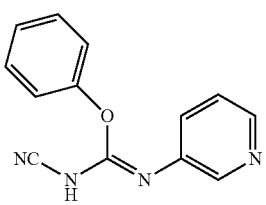 [SMILES: N#CN/C(=N/c1cccnc1)Oc1ccccc1] | 239 (M + 1) |
| 30 | 1-cyano-2-phenyl-3-(3-fluoro-pyridin-4-yl)isourea | 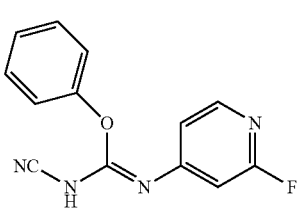 [SMILES: N#CN/C(=N/c1ccnc(F)c1)Oc1ccccc1] | 257 (M + 1) |

| Preparation number | Name of Compound | Structure | MS (m/z) |
|---|---|---|---|
| 31 | 1-cyano-2-phenyl-3-(3,5-difluoro-pyridin-4-yl)isourea | 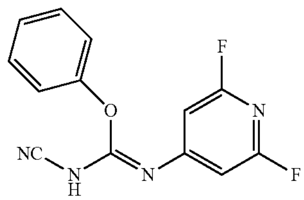 [SMILES: N#CN/C(=N/c1cc(F)nc(F)c1)Oc1ccccc1] | 275 (M + 1) |
| 31-1 | 1-cyano-2-phenyl-3-(3,5-dichloro-pyridin-4-yl)isourea | 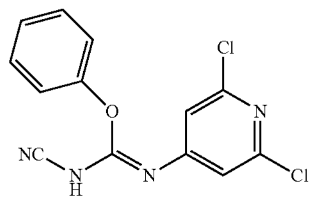 [SMILES: N#CN/C(=N/c1cc(Cl)nc(Cl)c1)Oc1ccccc1] | 307 (M + 1) |

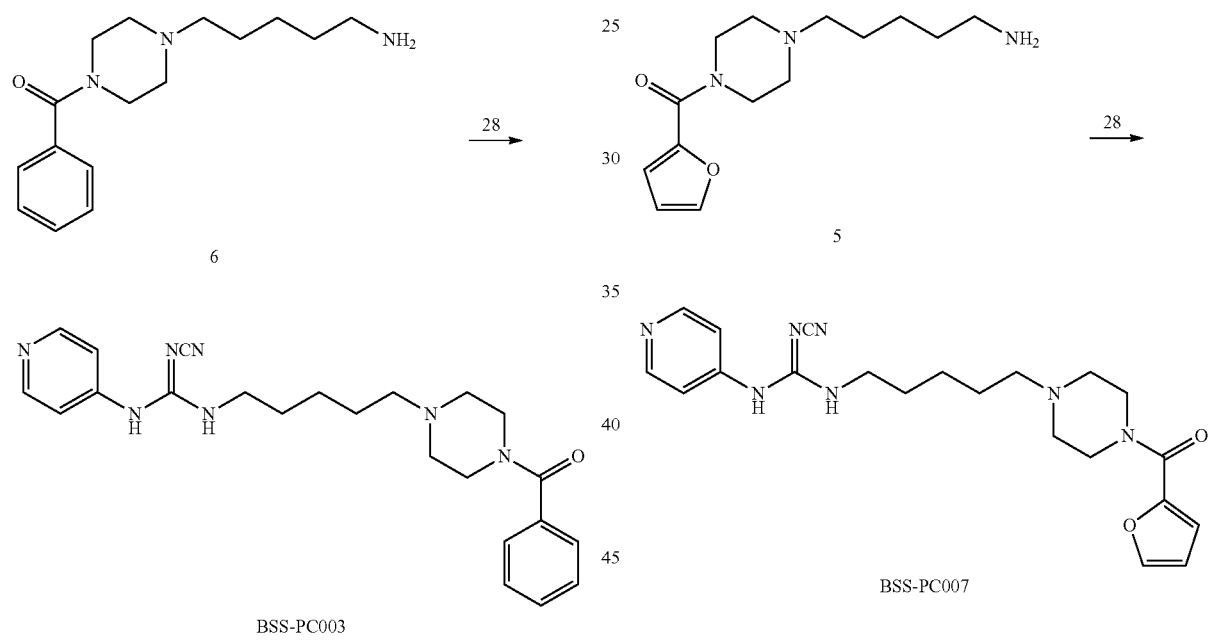

BSS-PC003

BSS-PC007

Example 13

35 mg of 1-cyano-2-phenyl-3-(pyridin-4-yl)isourea (28) and 50 mg of 1-benzoyl-4-(5'-amino-1'-pentyl)piperazine (6) was dissolved in 5 ml of acetonitrile, and 20.8 μl of triethyl amine was added and stirred overnight at 30° C. (30 hrs). The reaction solution was concentrated under reduced pressure, and directly separated by column chromatography (ethyl acetate/methanol=10:1-5:1 vol/vol, gradient elution), to obtain about 60 mg of a sticky target compound 2-cyano-1-(5-((1-(benzoyl)piperazine-4-yl)pentyl)-3-(4-pyridinyl)guanidine (BSS-PC 003). $^1$HNMR (400 MHz, CDCl3): δ=8.47-8.29 (m, 2H), 7.41-7.36 (d, 3H), 7.31-7.27 (m, 2H), 7.17-7.03 (m, 2H), 6.02-5.92 (m, 1H, N-H), 3.09-3.03 (m, 4H), 2.89-2.71 (m, 2H), 2.57-2.48 (m, 2H), 2.48-2.43 (m, 2H), 2.41-2.32 (m, 4H), 1.57-1.41 (m, 4H); [M+H]: 420.3.

Example 14

37 mg of 1-cyano-2-phenyl-3-(pyridin-4-yl)isourea (28) and 53 mg of 1-furoyl-4(5'-amino-1'-pentyl)piperazine (5) were dissolved in 5 ml of acetonitrile and then 20.8 μl of triethyl amine was added and stirred overnight at 30° C. (30 hrs). The reaction solution was concentrated under reduced pressure, and directly separated by column chromatography (ethyl acetate/methanol=10:1-5:1 vol/vol, gradient elution), to obtain about 72 mg of a sticky target compound 2-cyano-1-(5-((1-furoyl)piperazine-4-yl)pentyl)-3-(4-pyridinyl)guanidine (BSS-PC007). $^1$HNMR (400 MHz, CDCl3): δ=8.55-8.47 (m, 2H), 7.50-7.47 (d, 1H), 7.35-7.28 (m, 2H), 7.09-7.03 (d, 1H), 6.47-6.44 (m, 1H), 6.07-5.90 (m, 1H, N-H), 3.12-3.05 (m, 4H), 2.92-2.77 (m, 2H), 2.59-2.50 (m, 2H), 2.49-2.45 (m, 2H), 2.44-2.35 (m, 4H), 1.55-1.39 (m, 4H); [M+H]: 410.5.

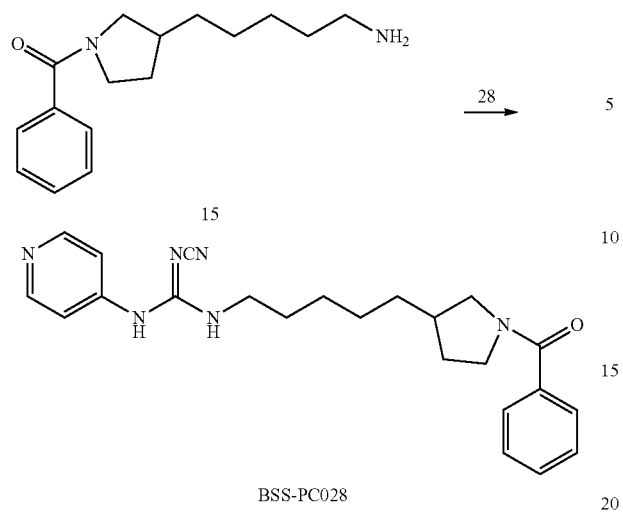

BSS-PC028

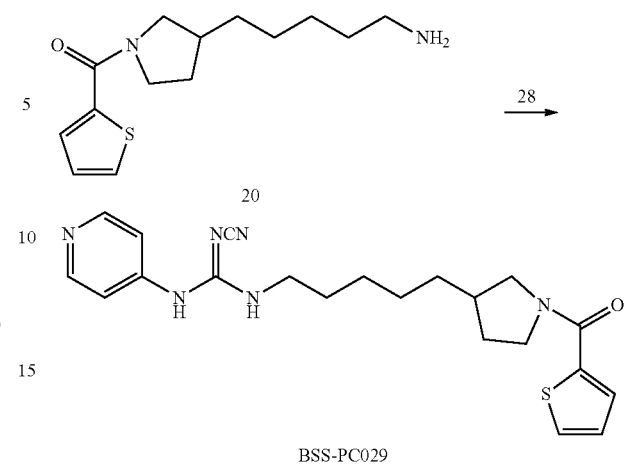

BSS-PC029

Example 15

36 mg of 1-cyano-2-phenyl-3-(pyridin-4-yl)isourea (28) and 51 mg of 1-benzoyl-3-(5'-amino-1'-pentyl)pyrrolidine (15) were dissolved in 5 ml of acetonitrile and then 20.8 μl of triethyl amine was added and stirred overnight at 30° C. (30 hrs). The reaction solution was concentrated under reduced pressure, and directly separated by column chromatography (dichloromethane/methanol vol/vol=10:1-5:1, gradient elution), to obtain about 63 mg of a sticky target compound 2-cyano-1-(5-((1-benzoyl)pyrrolidine-3-yl)pentyl)-3-(4-pyridinyl)guanidine(BSS-PC 028).

1HNMR (400 MHz, CDCl3): δ=8.42-8.21 (m, 2H), 7.37-7.30 (m, 3H), 7.29-7.26 (m, 2H), 7.16-7.04 (m, 2H), 6.04-5.83 (m, 1H, N-H), 4.11-3.95 (m, 2H), 3.89-3.74 (m, 2H), 3.65-3.11 (m, 3H), 2.29-1.92 (m, 2H), 1.70-1.53 (m, 2H), 1.47-1.32 (m, 4H), 1.32-1.19 (m, 2H); LC-MS: 405 [M-FH].

Example 16

34 mg of 1-cyano-2-phenyl-3-(pyridin-4-yl)isourea (28) and 50 mg of 1-(2-thienylformyl)-3-(5'-amino-1'-pentyl) pyrrolidine (20) were dissolved in 5 ml of acetonitrile and then 22 μl of triethyl amine was added, and stirred overnight at 30° C. (30 hrs). The reaction solution was concentrated under reduced pressure, and directly separated by column chromatography (dichloromethane/methanol vol/vol=10:1-5:1, gradient elution), to obtain about 40 mg of a sticky target compound 2-cyano-1-(5-(1-(2-thienylformyl)pyrrolidine-3-yl)pentyl)-3-(4-pyridinyl)guanidine(BSS-PCO29).

1HNMR (400 MHz, CDCl3): δ=8.60-8.31 (m, 2H), 7.46-7.42 (1H), 7.30-7.18 (m, 3H), 7.07-7.01 (m, 1H), 6.09-5.99 (m, 1H, N-H), 4.09-3.92 (m, 2H), 3.88-3.73 (m, 2H), 3.60-3.15 (m, 3H), 2.32-1.95 (m, 2H), 1.67-1.51 (m, 2H), 1.49-1.29 (m, 4H), 1.33-1.18 (m, 2H); LC-MS: 411[M+H].

The following compounds can be prepared according to the above method of preparing the compound BSS-PC003 starting from the compounds 6 and 28:

| Preparation number | Name of Compound | Structure | MS (m/z) |
|---|---|---|---|
| BSS-PC006 | 2-cyano-1-(5-(1-(2,6-dimethoxybenzoyl)piperazine-4-yl)pentyl)-3-(4-pyridinyl)guanidine | 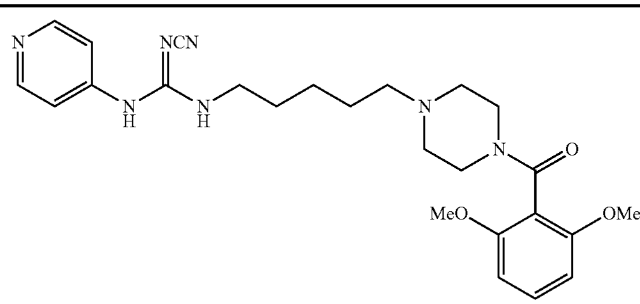 | 480 (M + 1) |
| BSS-PC004 | 2-cyano-1-(5-(1-(2-thienylformyl)piperazine-4-yl)pentyl)-3-(4-pyridinyl)guanidine | 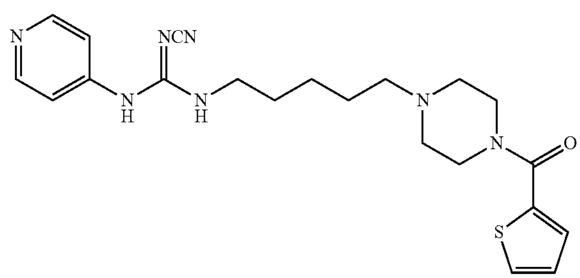 | 426 (M + 1) |

-continued

| Preparation number | Name of Compound | Structure | MS (m/z) |
|---|---|---|---|
| BSS-PC005 | 2-cyano-1-(5-((1-benzoyl)piperazine-4-yl)pentyl)-3-(3-fluoro-4-pyridinyl)guanidine | 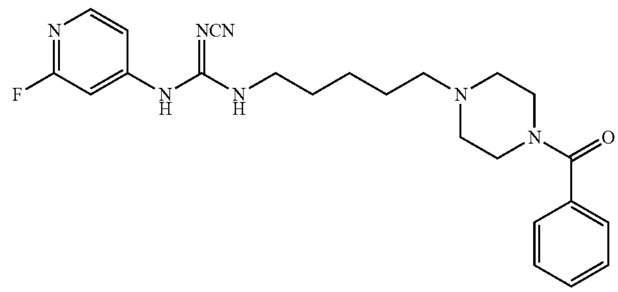 | 438 (M + 1) |
| BSS-PC008 | 2-cyano-1-(5-(1-(2-pyrrolylformyl)piperazine-4-yl)pentyl)-3-(4-pyridinyl)guanidine | 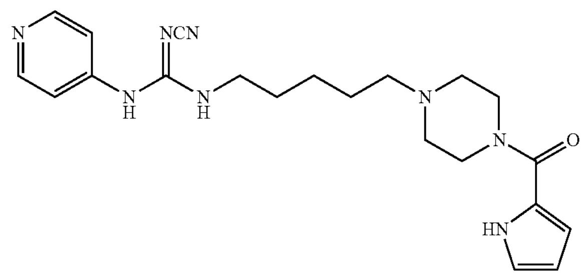 | 409 (M + 1) |
| BSS-PC010 | 2-cyano-1-(5-(1-(2-pyrrolidinylformyl)piperazine-4-yl)pentyl)-3-(4-pyridinyl)guanidine | 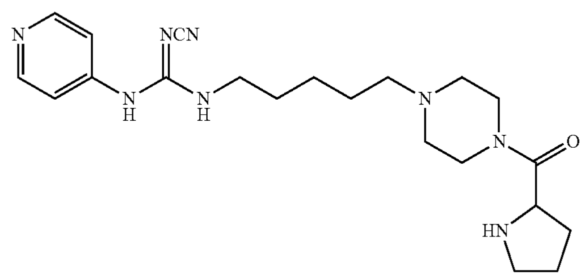 | 413 (M + 1) |
| BSS-PC011 | 2-cyano-1-(5-(1-(2-tetrahydrofurylfuryl)piperazine-4-yl)pentyl)-3-(4-pyridinyl)guanidine | 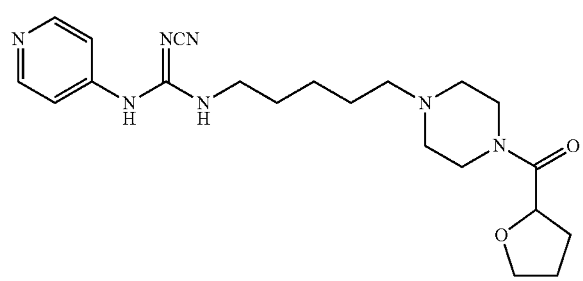 | 414 (M + 1) |
| BSS-PC009 | 2-cyano-1-(5-(1-(2-tetrahydrothienylformyl)piperazine-4-yl)pentyl)-3-(4-pyridinyl)guanidine | 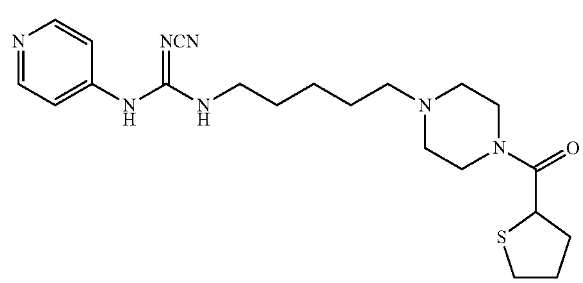 | 430 (M + 1) |

-continued

| Preparation number | Name of Compound | Structure | MS (m/z) |
|---|---|---|---|
| BSS-PC012 | 2-cyano-1-(5-(1-(2,6-dimethoxybenzoyl)piperazine-4-yl)pentyl)-3-(3-fluoro-4-pyridinyl)guanidine | 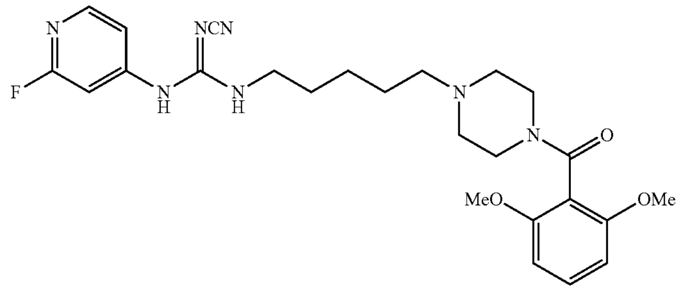 | 498 (M + 1) |
| BSS-PC013 | 2-cyano-1-(5-((1-furoyl)piperazine-4-yl)pentyl)-3-(3-fluoro-4-pyridinyl)guanidine | 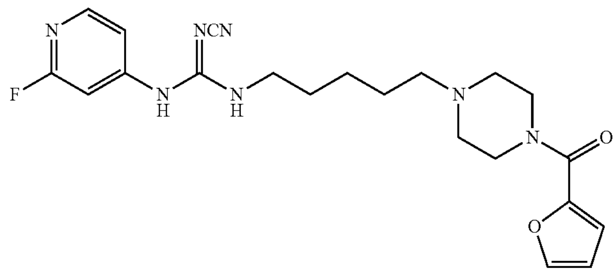 | 428 (M + 1) |
| BSS-PC014 | 2-cyano-1-(5-(1-(2-pyrrolylformyl)piperazine-4-yl)pentyl)-3-(3-fluoro-4-pyridinyl)guanidine | 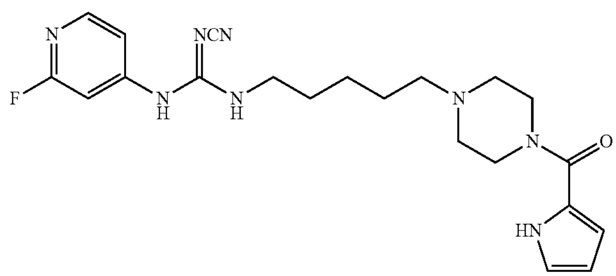 | 427 (M + 1) |
| BSS-PC015 | 2-cyano-1-(5-((1-benzoyl)piperazine-4-yl)pentyl)-3-(3,5-difluoro-4-pyridinyl)guanidine | 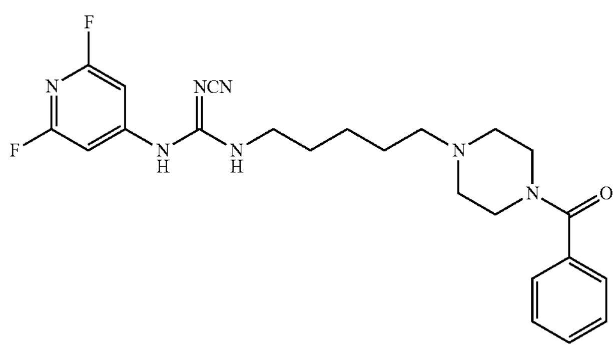 | 456 (M + 1) |
| BSS-PC016 | 2-cyano-1-(5-(1-(2-pyrrolidinylformyl)piperazine-4-yl)pentyl)-3-(3-fluoro-4-pyridinyl)guanidine | 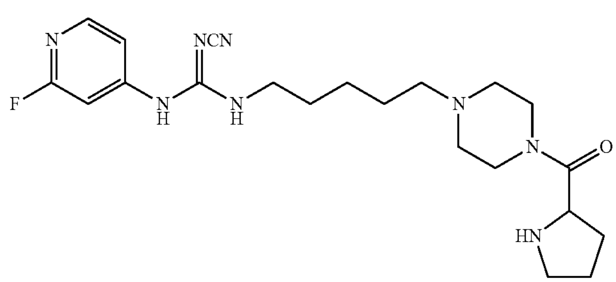 | 431 (M + 1) |

-continued

| Preparation number | Name of Compound | Structure | MS (m/z) |
|---|---|---|---|
| BSS-PC017 | 2-cyano-1-(5-(1-(2-thienylformyl)piperazine-4-yl)pentyl)-3-(3-fluoro-4-pyridinyl)guanidine | 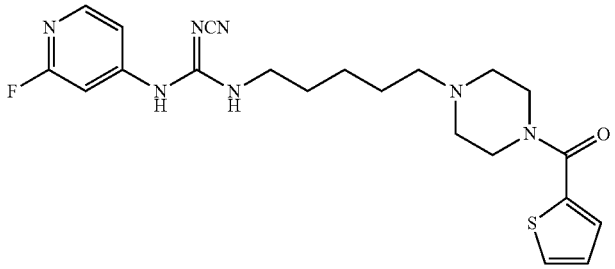 | 444 (M + 1) |
| BSS-PC018 | 2-cyano-1-(5-(1-(2-thienylformyl)piperazine-4-yl)pentyl)-3-(3-pyridinyl)guanidine | 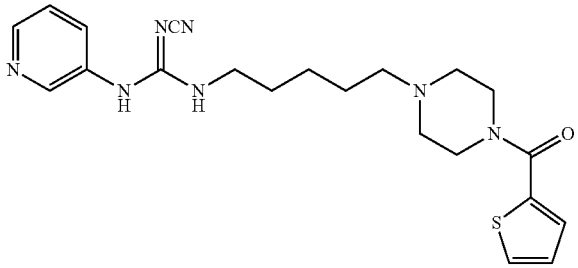 | 426 (M + 1) |
| BSS-PC019 | 2-cyano-1-(5-((1-benzoyl)piperazine-4-yl)pentyl)-3-(3-pyridinyl)guanidine | 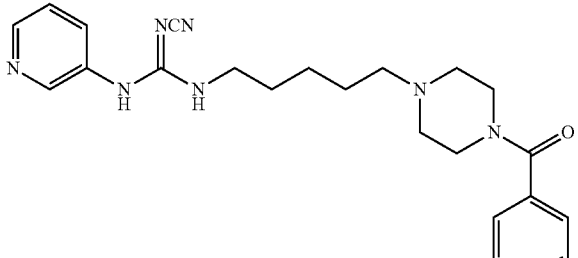 | 420 (M + 1) |
| BSS-PC020 | 2-cyano-1-(5-(1-(2-indolylformyl)piperazine-4-yl)pentyl)-3-(4-pyridinyl)guanidine | 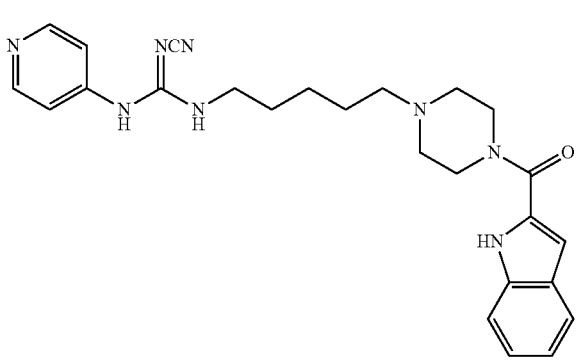 | 459 (M + 1) |
| BSS-PC021 | 2-cyano-1-(5-(1-(2-benzotetrahydrofurylfuryl)piperazine-4-yl)pentyl)-3-(4-pyridinyl)guanidine | 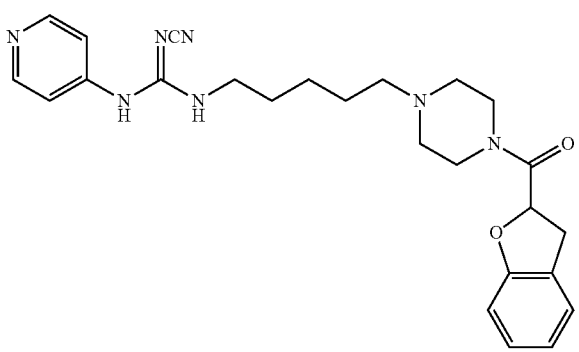 | 462 (M + 1) |

-continued

| Preparation number | Name of Compound | Structure | MS (m/z) |
|---|---|---|---|
| BSS-PC022 | 2-cyano-1-(5-(1-(2-benzofurylformyl)piperazine-4-yl)pentyl)-3-(4-pyridinyl)guanidine | 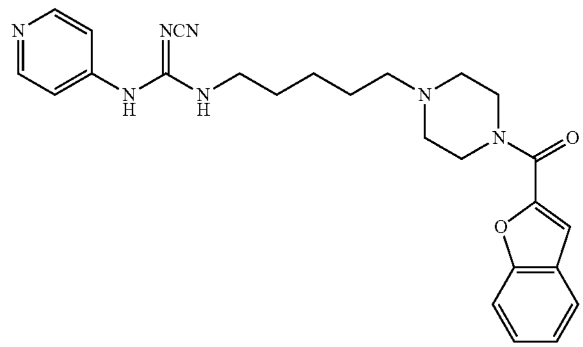 | 460 (M + 1) |
| BSS-PC023 | 2-cyano-1-(5-(1-(3-fluoro-2-furylformyl)piperazine-4-yl)pentyl)-3-(4-pyridinyl)guanidine | 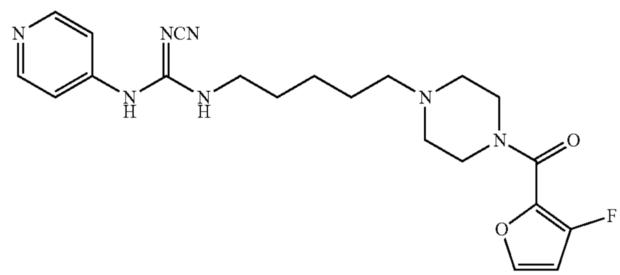 | 428 (M + 1) |
| BSS-PC024 | 2-cyano-1-(5-(1-(3-fluoro-2-pyrrolylformyl)piperazine-4-yl)pentyl)-3-(4-pyridinyl)guanidine | 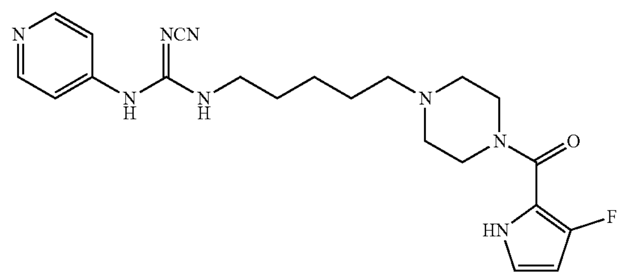 | 427 (M + 1) |
| BSS-PC025 | 2-cyano-1-(5-(1-(3-fluoro-2-thienylformyl)piperazine-4-yl)pentyl)-3-(4-pyridinyl)guanidine | 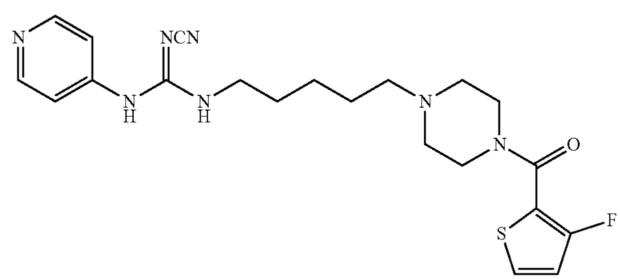 | 444 (M + 1) |
| BSS-PC026 | 2-cyano-1-(5-((1-furoyl)piperazine-4-yl)pentyl)-3-(3-pyridinyl)guanidine | 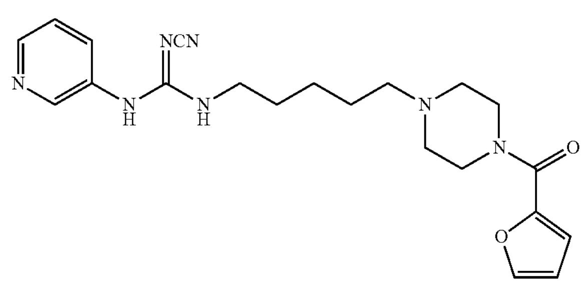 | 410 (M + 1) |

-continued

| Preparation number | Name of Compound | Structure | MS (m/z) |
|---|---|---|---|
| BSS-PC027 | 2-cyano-1-(5-(1-(2,6-dimethoxybenzoyl)piperazine-4-yl)pentyl)-3-(3-pyridinyl)guanidine | 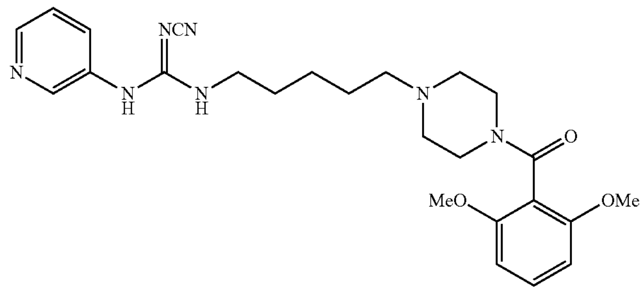 | 480 (M + 1) |
| BSS-PC030 | 2-cyano-1-(5-((1-benzoyl)pyrrolidine-3-yl)pentyl)-3-(3-fluoro-4-pyridinyl)guanidine | 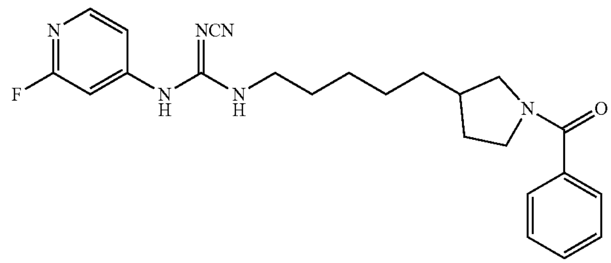 | 423 (M + 1) |
| BSS-PC031 | 2-cyano-1-(5-(1-(2,6-dimethoxybenzoyl)pyrrolidine-3-yl)pentyl)-3-(4-pyridinyl)guanidine | 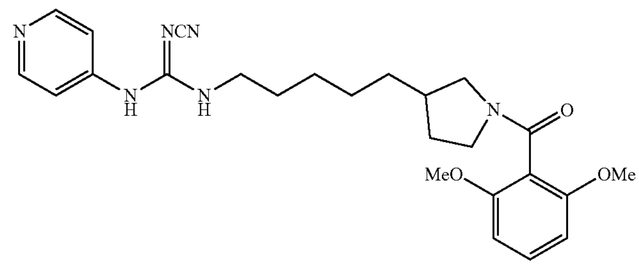 | 465 (M + 1) |
| BSS-PC032 | 2-cyano-1-(5-(1-(furoyl)pyrrolidine-3-yl)pentyl)-3-(4-pyridinyl)guanidine | 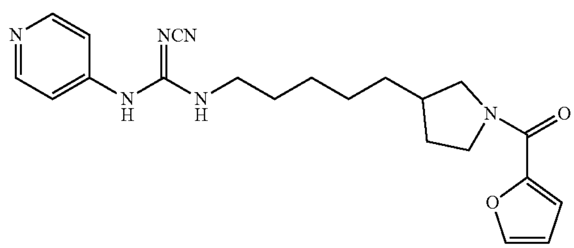 | 395 (M + 1) |
| BSS-PC033 | 2-cyano-1-(5-(1-(2-pyrrolylformyl)pyrrolidine-3-yl)pentyl)-3-(4-pyridinyl)guanidine | 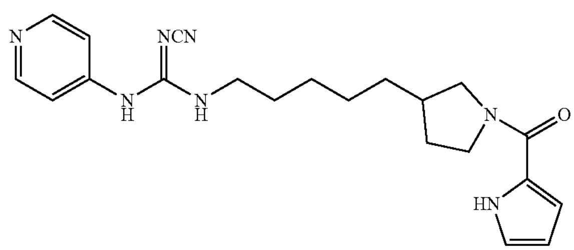 | 394 (M + 1) |
| BSS-PC035 | 2-cyano-1-(5-(1-(2-pyrrolidinylformyl)pyrrolidine-3-yl)pentyl)-3-(4-pyridinyl)guanidine | 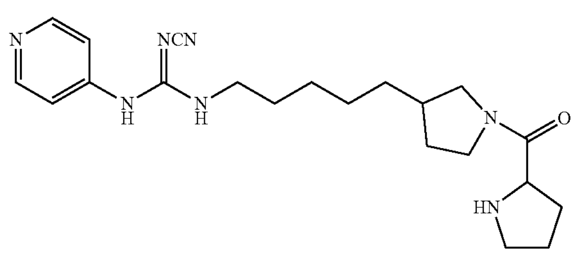 | 398 (M + 1) |

-continued

| Preparation number | Name of Compound | Structure | MS (m/z) |
|---|---|---|---|
| BSS-PC036 | 2-cyano-1-(5-(1-(2-tetrahydrofuranformyl)pyrrolidine-3-yl)pentyl)-3-(4-pyridinyl)guanidine | 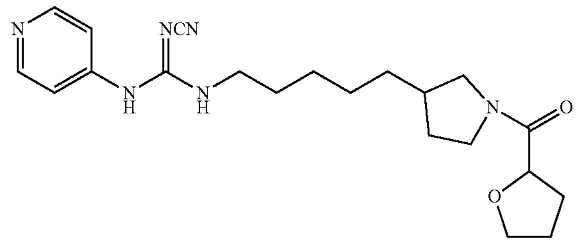 | 399 (M + 1) |
| BSS-PC034 | 2-cyano-1-(5-(1-(2-tetrahydrothienylformyl)pyrrolidine-3-yl)pentyl)-3-(4-pyridinyl)guanidine | 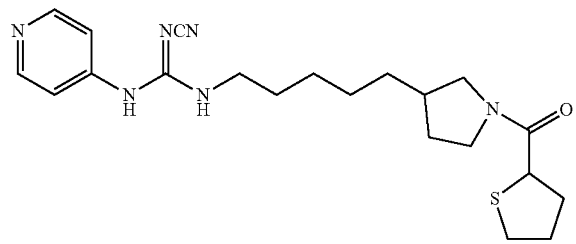 | 415 (M + 1) |
| BSS-PC037 | 2-cyano-1-(5-(1-(2,6-dimethoxybenzoyl)pyrrolidine-3-yl)pentyl)-3-(3-fluoro-4-pyridinyl)guanidine | 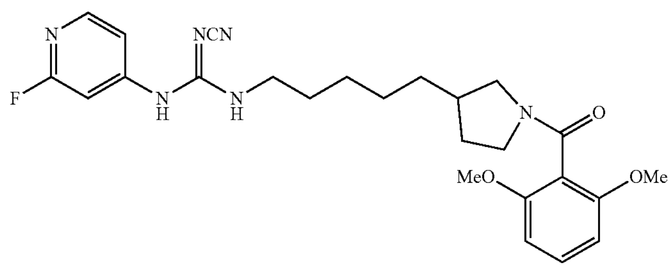 | 483 (M + 1) |
| BSS-PC038 | 2-cyano-1-(5-(1-(furoyl)pyrrolidine-3-yl)pentyl)-3-(3-fluoro-4-pyridinyl)guanidine | 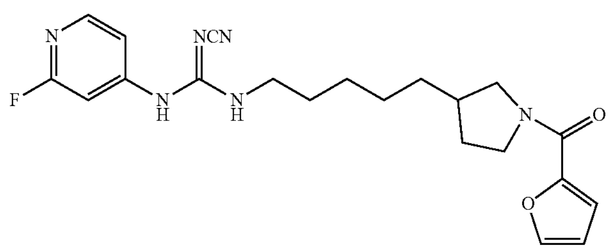 | 413 (M + 1) |
| BSS-PC039 | 2-cyano-1-(5-(1-(2-pyrrolylformyl)pyrrolidine-3-yl)pentyl)-3-(3-fluoro-4-pyridinyl)guanidine | 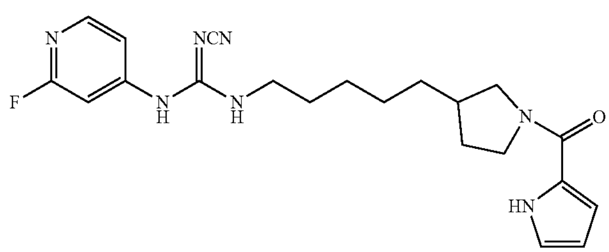 | 412 (M + 1) |
| BSS-PC040 | 2-cyano-1-(5-((1-benzoyl)pyrrolidine-3-yl)pentyl)-3-(3,5-difluoro-4-pyridinyl)guanidine | 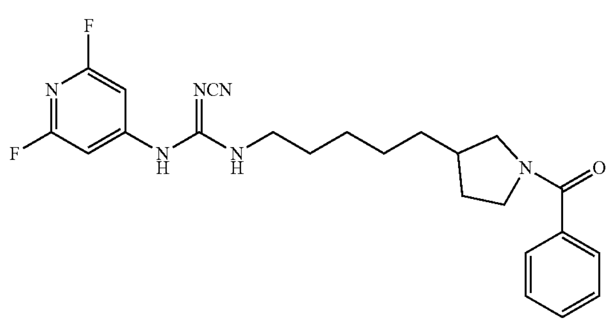 | 441 (M + 1) |

-continued

| Preparation number | Name of Compound | Structure | MS (m/z) |
|---|---|---|---|
| BSS-PC041 | 2-cyano-1-(5-(1-(2-pyrrolidinylformyl)pyrrolidine-3-yl)pentyl)-3-(3-fluoro-4-pyridinyl)guanidine | 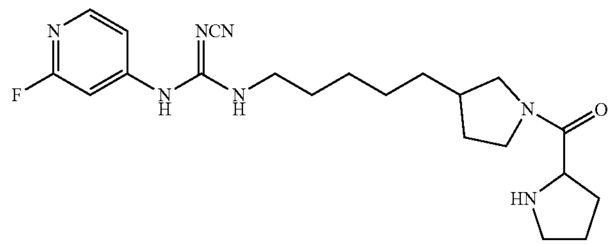 | 416 (M + 1) |
| BSS-PC042 | 2-cyano-1-(5-(1-(2-thienylformyl)pyrrolidine-3-yl)pentyl)-3-(3-fluoro-4-pyridinyl)guanidine | 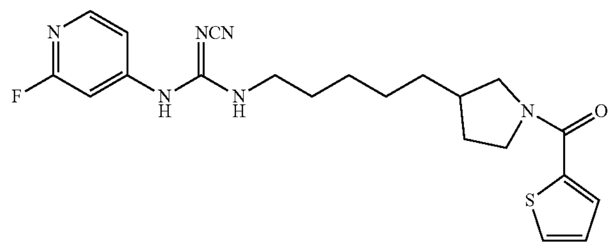 | 429 (M + 1) |
| BSS-PC043 | 2-cyano-1-(5-(1-(2-thienylformyl)pyrrolidine-3-yl)pentyl)-3-(3-pyridinyl)guanidine | 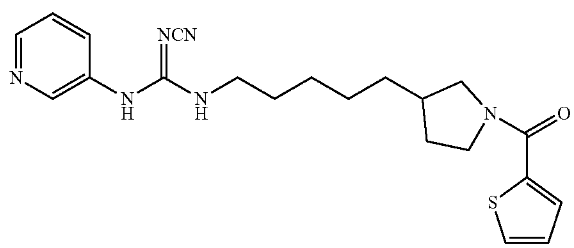 | 411 (M + 1) |
| BSS-PC044 | 2-cyano-1-(5-((1-benzoyl)pyrrolidine-3-yl)pentyl)-3-(3-pyridinyl)guanidine | 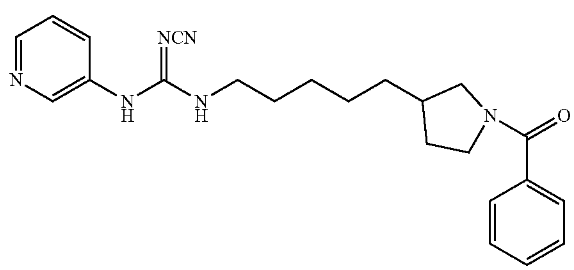 | 405 (M + 1) |
| BSS-PC045 | 2-cyano-1-(5-(1-(2-indolylformyl)pyrrolidine-3-yl)pentyl)-3-(4-pyridinyl)guanidine | 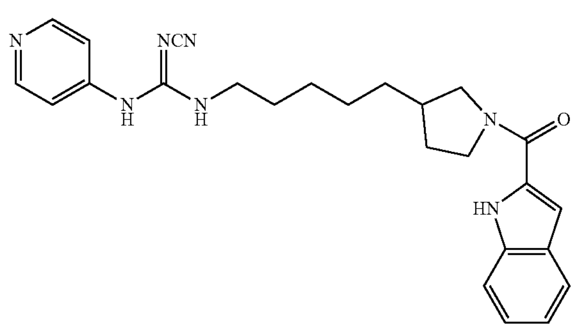 | 444 (M + 1) |

-continued

| Preparation number | Name of Compound | Structure | MS (m/z) |
|---|---|---|---|
| BSS-PC046 | 2-cyano-1-(5-(1-(2-benzotetrahydrofurylfuryl) pyrrolidine-3-yl) pentyl)-3-(4-pyridinyl)guanidine | 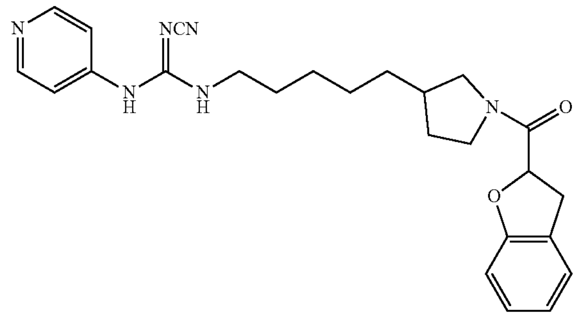 | 447 (M + 1) |
| BSS-PC047 | 2-cyano-1-(5-(1-(2-benzofurylformyl) pyrrolidine-3-yl)pentyl)-3-(4-pyridinyl)guanidine | 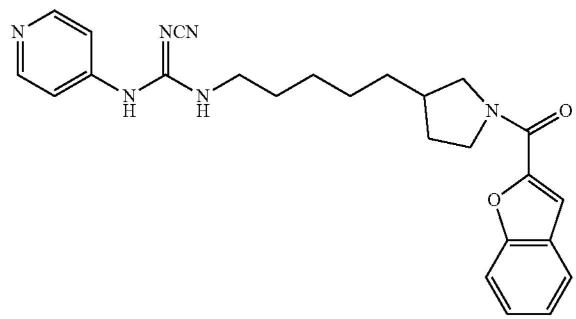 | 445 (M + 1) |
| BSS-PC048 | 2-cyano-1-(5-(1-(3-fluoro-2-furylformyl)pyrrolidine-3-yl)pentyl)-3-(4-pyridinyl)guanidine | 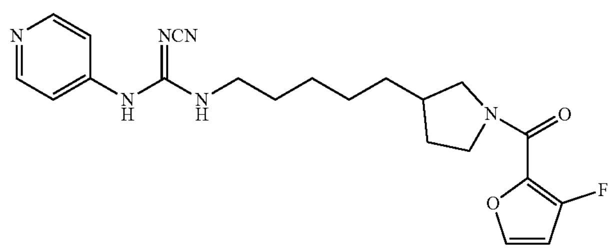 | 413 (M + 1) |
| BSS-PC049 | 2-cyano-1-(5-(1-(3-fluoro-2-pyrrolylformyl) pyrrolidine-3-yl)pentyl)-3-(4-pyridinyl)guanidine | 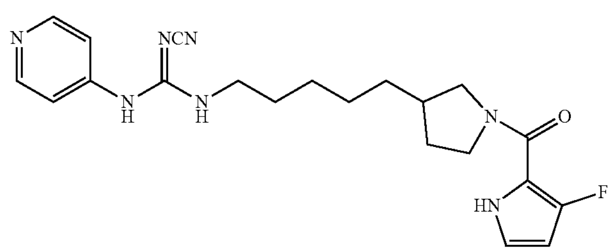 | 412 (M + 1) |
| BSS-PC050 | 2-cyano-1-(5-(1-(3-fluoro-2-thienylformyl) pyrrolidine-3-yl)pentyl)-3-(4-pyridinyl)guanidine | 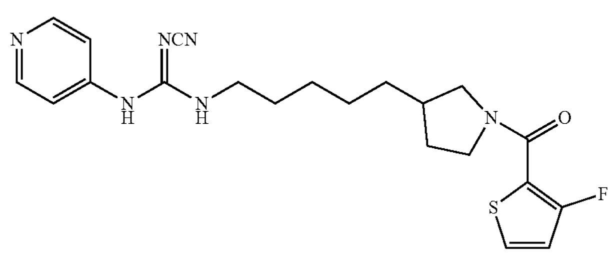 | 429 (M + 1) |

-continued

| Preparation number | Name of Compound | Structure | MS (m/z) |
|---|---|---|---|
| BSS-PC051 | 2-cyano-1-(5-((1-furoyl)pyrrolidine-3-yl)pentyl)-3-(4-pyridinyl)guanidine | 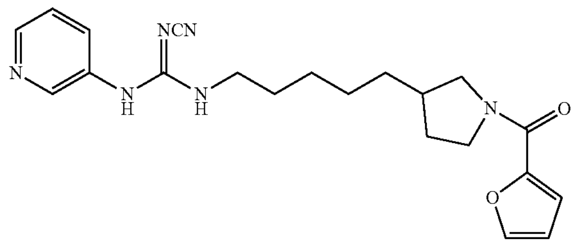 | 395 (M + 1) |
| BSS-PC052 | 2-cyano-1-(5-(1-(2,6-dimethoxybenzoyl)pyrrolidine-3-yl)pentyl)-3-(3-pyridinyl)guanidine | 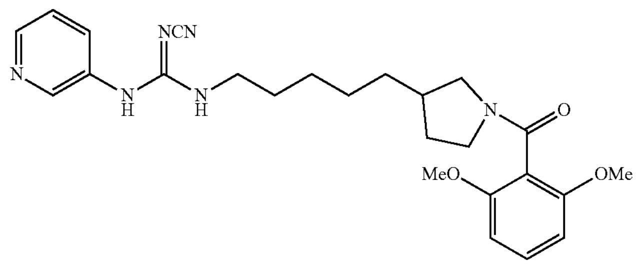 | 465 (M + 1) |
| BSS-PC054 | 2-cyano-1-(6-((1-benzoyl)pyrrolidine-3-yl)hexyl)-3-(4-pyridinyl)guanidine | 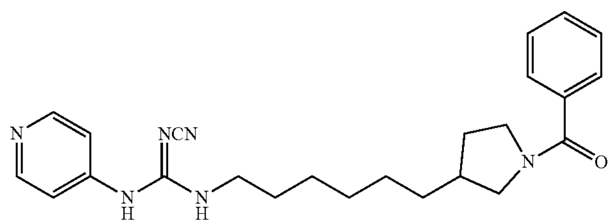 | 419 (M + 1) |
| BSS-PC055 | 2-cyano-1-(6-(1-(2,6-dimethoxybenzoyl)pyrrolidine-3-yl)hexyl)-3-(4-pyridinyl)guanidine | 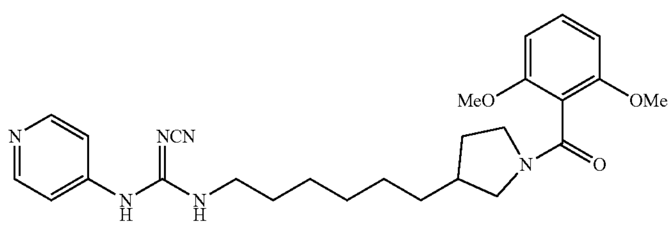 | 479 (M + 1) |
| BSS-PC053 | 2-cyano-1-(6-(1-(2-thienylformyl)pyrrolidine-3-yl)hexyl)-3-(4-pyridinyl)guanidine | 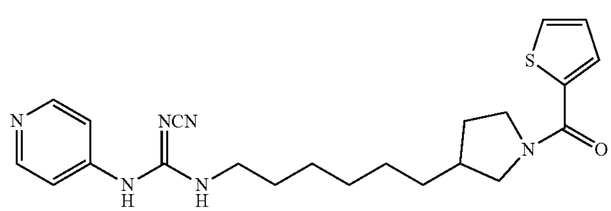 | 425 (M + 1) |
| BSS-PC056 | 2-cyano-1-(6-(1-(2-pyrrolylformyl)pyrrolidine-3-yl)hexyl)-3-(4-pyridinyl)guanidine | 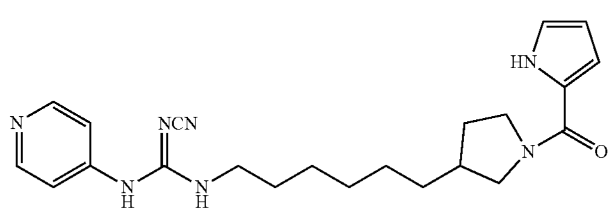 | 408 (M + 1) |

-continued

| Preparation number | Name of Compound | Structure | MS (m/z) |
|---|---|---|---|
| BSS-PC057 | 2-cyano-1-(6-(1-(furoyl)pyrrolidine-3-yl)hexyl)-3-(4-pyridinyl)guanidine | 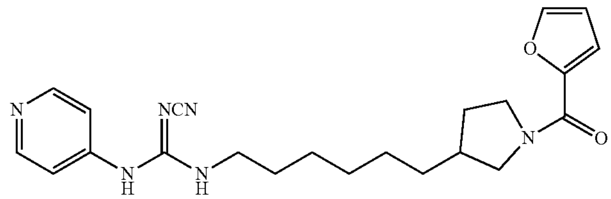 | 409 (M + 1) |
| BSS-PC058 | 2-cyano-1-(6-(1-(2-tetrahydrothienylformyl)pyrrolidine-3-yl)hexyl)-3-(4-pyridinyl)guanidine | 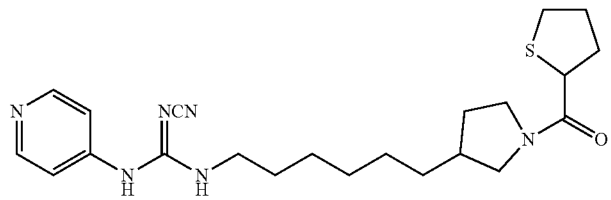 | 429 (M + 1) |
| BSS-PC059 | 2-cyano-1-(6-((1-benzoyl)pyrrolidine-3-yl)hexyl)-3-(3-pyridinyl)guanidine | 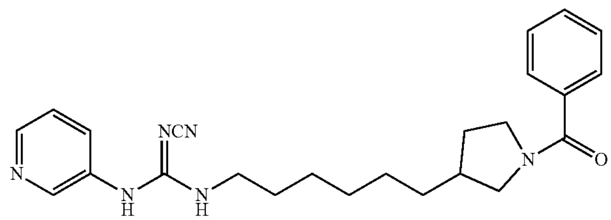 | 419 (M + 1) |
| BSS-PC062 | 2-cyano-1-(6-(1-(furoyl)pyrrolidine-3-yl)hexyl)-3-(3-pyridinyl)guanidine | 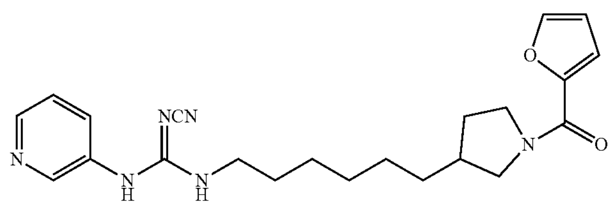 | 409 (M + 1) |
| BSS-PC060 | 2-cyano-1-(6-(1-(2-thienylformyl)pyrrolidine-3-yl)hexyl)-3-(3-pyridinyl)guanidine | 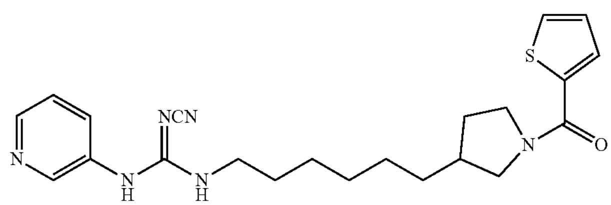 | 425 (M + 1) |
| BSS-PC061 | 2-cyano-1-(6-(1-(2-pyrrolylformyl)pyrrolidine-3-yl)hexyl)-3-(3-pyridinyl)guanidine | 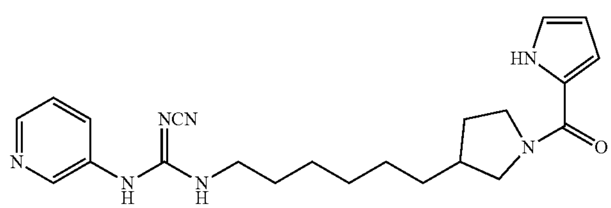 | 408 (M + 1) |
| BSS-PC063 | 2-cyano-1-(6-(1-(2-tetrahydrothienylformyl)pyrrolidine-3-yl)hexyl)-3-(3-pyridinyl)guanidine | 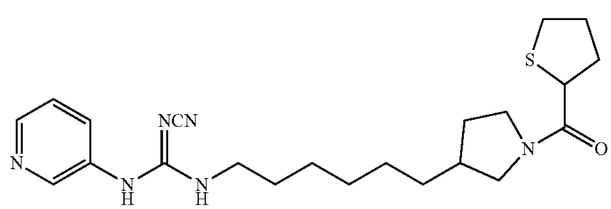 | 429 (M + 1) |

-continued

| Preparation number | Name of Compound | Structure | MS (m/z) |
|---|---|---|---|
| BSS-PC064 | 2-cyano-1-(6-((1-benzoyl)pyrrolidine-3-yl)hexyl)-3-(3-fluoro-4-pyridinyl)guanidine | 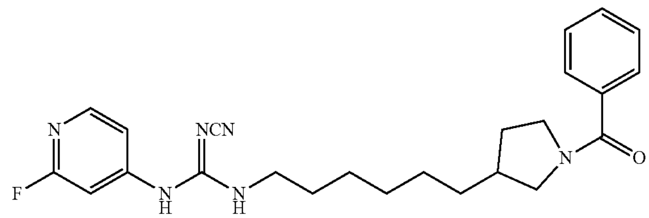 | 437 (M + 1) |
| BSS-PC065 | 2-cyano-1-(6-(1-(2,6-dimethoxybenzoyl)pyrrolidine-3-yl)hexyl)-3-(3-fluoro-4-pyridinyl)guanidine | 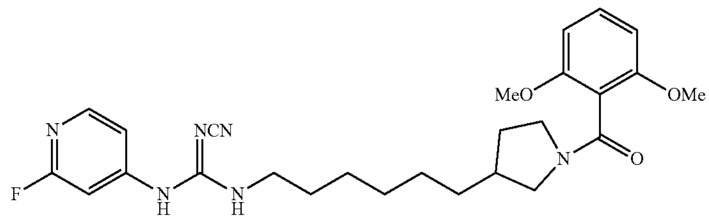 | 497 (M + 1) |
| BSS-PC067 | 2-cyano-1-(6-(1-(2-pyrrolylformyl)pyrrolidine-3-yl)hexyl)-3-(3-fluoro-4-pyridinyl)guanidine | 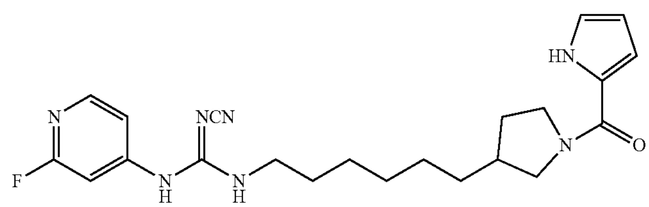 | 426 (M + 1) |
| BSS-PC068 | 2-cyano-1-(6-(1-(furoyl)pyrrolidine-3-yl)hexyl)-3-(3-fluoro-4-pyridinyl)guanidine | 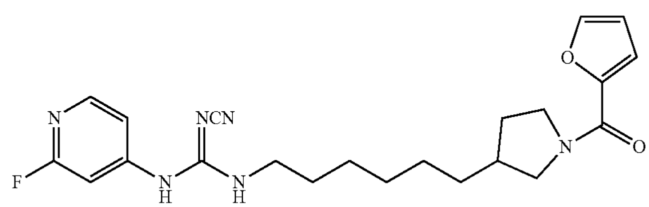 | 427 (M + 1) |
| BSS-PC066 | 2-cyano-1-(6-(1-(2-thienylformyl)pyrrolidine-3-yl)hexyl)-3-(3-fluoro-4-pyridinyl)guanidine | 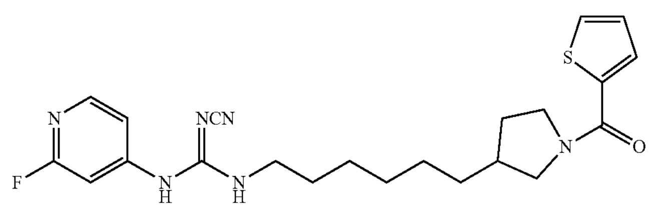 | 443 (M + 1) |
| BSS-PC069 | 2-cyano-1-(6-(1-(2-tetrahydrothienylformyl)pyrrolidine-3-yl)hexyl)-3-(3-fluoro-4-pyridinyl)guanidine | 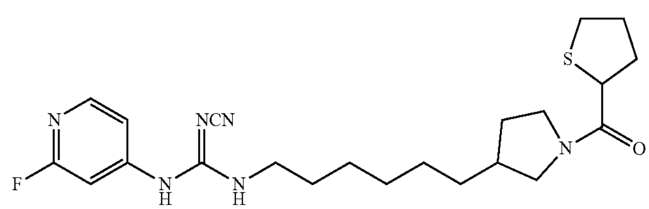 | 447 (M + 1) |
| BSS-PC070 | 2-cyano-1-(6-(1-(2-pyrrolidinylformyl)pyrrolidin 3-yl)hexyl)-3-(3-fluoro-4-pyridinyl)guanidine | 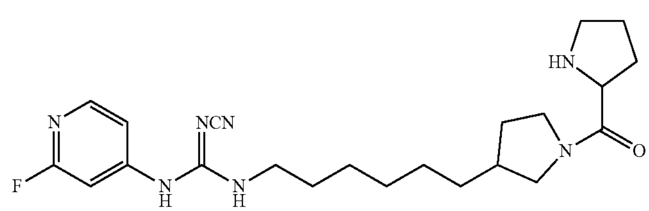 | 430 (M + 1) |

-continued

| Preparation number | Name of Compound | Structure | MS (m/z) |
|---|---|---|---|
| BSS-PC071 | 2-cyano-1-(6-(1-(2-indolylformyl)pyrrolidine-3-yl)hexyl)-3-(4-pyridinyl)guanidine | 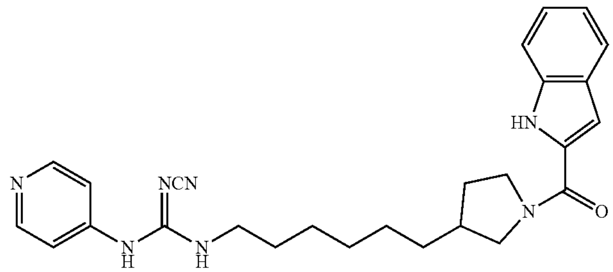 | 458 (M + 1) |
| BSS-PC072 | 2-cyano-1-(6-(1-(2-benzofurylformyl)pyrrolidine-3-yl)hexyl)-3-(4-pyridinyl)guanidine | 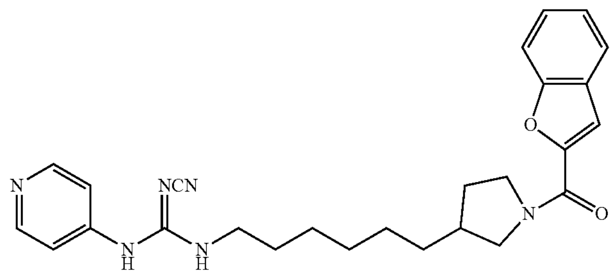 | 459 (M + 1) |
| BSS-PC073 | 2-cyano-1-(6-((1-benzoyl)pyrrolidine-3-yl)hexyl)-3-(3,5-difluoro-4-pyridinyl)guanidine | 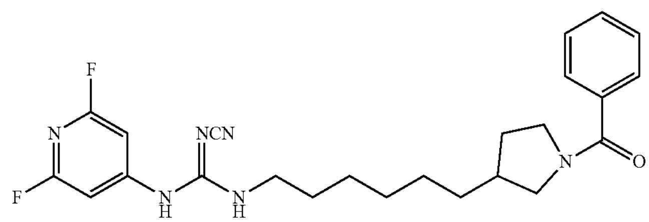 | 455 (M + 1) |
| BSS-PC074 | 2-cyano-1-(6-(1-(2,6-dimethoxybenzoyl)pyrrolidine-3-yl)hexyl)-3-(3,5-difluoro-4-pyridinyl)guanidine | 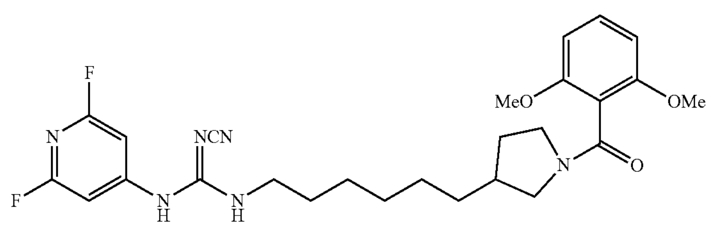 | 515 (M + 1) |
| BSS-PC075 | 2-cyano-1-(6-(1-(2-thienylformyl)pyrrolidine-3-yl)hexyl)-3-(3,5-difluoro-4-pyridinyl)guanidine | 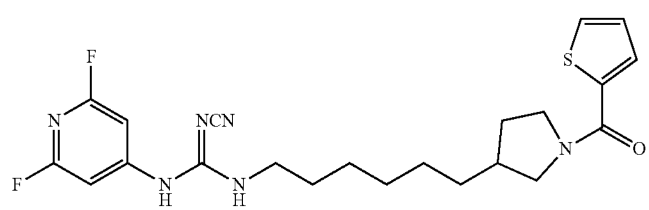 | 461 (M + 1) |
| BSS-PC076 | 2-cyano-1-(6-((1-furoyl)pyrrolidine-3-yl)hexyl)-3-(3,5-difluoro-4-pyridinyl)guanidine | 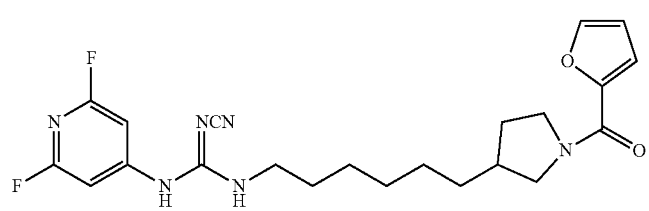 | 445 (M + 1) |

-continued

| Preparation number | Name of Compound | Structure | MS (m/z) |
|---|---|---|---|
| BSS-PC077 | 2-cyano-1-(6-(1-(2-pyrrolylformyl)pyrrolidine-3-yl)hexyl)-3-(3,5-difluoro-4-pyridinyl)guanidine | 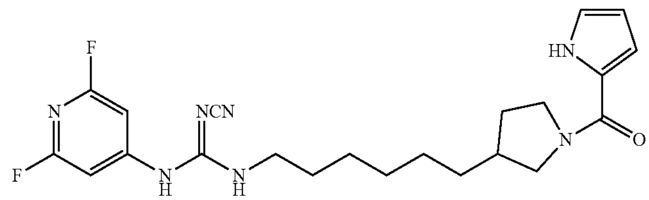 | 444 (M + 1) |
| BSS-PC078 | 2-cyano-1-(6-(1-(2-thienylformyl)pyrrolidine-3-yl)hexyl)-3-(3,5-dichloro-4-pyridinyl)guanidine | 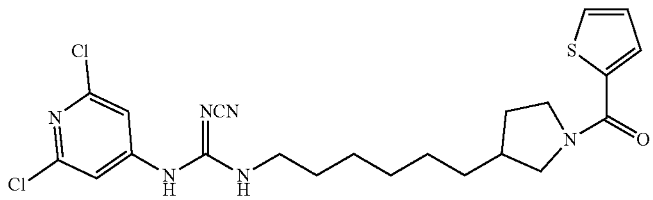 | 493 |
| BSS-PC079 | 2-cyano-1-(6-(1-(2-pyrrolylformyl)pyrrolidine-3-yl)hexyl)-3-(3,5-dichloro-4-pyridinyl)guanidine | 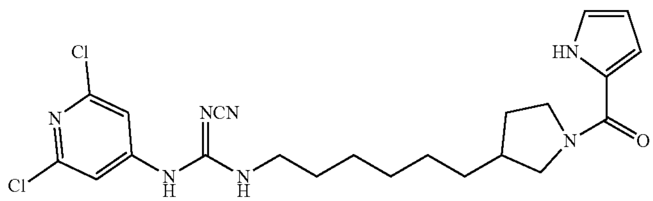 | 476 (M + 1) |
| BSS-PC080 | 2-cyano-1-(6-((1-furoyl)pyrrolidine-3-yl)hexyl)-3-(3,5-dichloro-4-pyridinyl)guanidine | 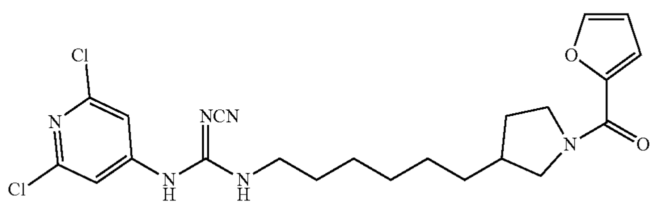 | 477 (M + 1) |
| BSS-PC081 | 2-cyano-1-(6-((1-benzoyl)pyrrolidine-3-yl)hexyl)-3-(3,5-dichloro-4-pyridinyl)guanidine | 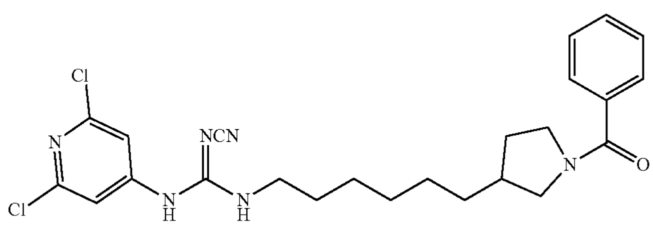 | 487 (M + 1) |

Example 17

The effect of samples on the proliferation of human tumor cells in vitro was determined by CCK-8 cell proliferation assay.

TABLE 1

| Cell line | Cell lines and culture conditions | | | |
|---|---|---|---|---|
| | Complete growth medium | | Temperature | Atmosphere |
| | base medium | serum | | air / CO$_2$ |
| Human lung adenocarcinoma cell A549 | RPMI-1640 | FBS | 37° C. | 95% 5% |
| Human hepatoma cell HepG2 | MEM | FBS | 37° C. | 95% 5% |
| Human esophageal cancer cell TE-1 | DMEM | FBS | 37° C. | 95% 5% |
| Human gastric cancer cell MKN45 | RPMI-1640 | FBS | 37° C. | 95% 5% |
| Human colon cancer cell HCT-116 | McCoy's 5A | FBS | 37° C. | 95% 5% |
| Human multiple myeloma cell RPMI 8226 | RPMI-1640 | FBS | 37° C. | 95% 5% |
| Human pancreatic cancer cell CFPAC-1 | DMEM | FBS | 37° C. | 95% 5% |
| Human pancreatic cancer cell PANC-1 | DMEM | FBS | 37° C. | 95% 5% |

The cells were assayed through a method including the following steps:
1) The cells were digested, counted, and prepared into a cell suspension in a corresponding culture medium (Table 1) (5×10⁴ cells/ml for CFPAC-1 and RPMI 8226, and 3.5×10⁴ cells/ml for rest cells). The cell suspension was added to each well of a 96-well plate in 100 μl/well.
2) Then the 96-well plate was incubated for 24 hrs in an incubator at 37° C. and 5% $CO_2$.
3) The drug was diluted with the culture medium to the required working concentration. 100 μl of the corresponding drug containing medium was added to each well. A negative control group (added with drug-free culture medium) was also set.
4) Then the 96-well plate was incubated for 72 hrs in an incubator at 37° C. and 5% $CO_2$.
5) The 96-well plate was stained with CCK-8, and The OD value was determined at λ=450 nm.
  1) 10 μl of CCK-8 was added to each well, and incubated in the incubator for another 2-3 hrs.
  2) The content was mixed uniformly by shaking gently on a shaker for 10 min, and the bubbles in the 96-well plate were removed.
  3) The OD value of each well was read on a plate reader at λ=450 nm, and the inhibition rate was calculated.
6) The inhibition rate in each group was calculated.

$$\text{Inhibition (\%)} = \frac{\text{OD value of negative control group} - \text{OD value of experimental group}}{\text{OD value of negative control group}} \times 100\%$$

The data of cell assay are shown in the following table:

| Drug number | A549 | HepG2 | TE-1 | MKN-45 | HCT116 | RPMI8226 | CFPAC-1 |
|---|---|---|---|---|---|---|---|
| FK866 | 0.037 | 0.099 | 0.112 | 0.039 | 0.092 | 0.02 | 0.037 |
| BSS-PC003 | 0.029 | 0.049 | 0.046 | 0.050 | 0.041 | 0.019 | 0.026 |
| BSS-PC004 | 0.035 | 0.082 | 0.095 | 0.043 | 0.066 | 0.034 | 0.025 |
| BSS-PC005 | 0.035 | 0.123 | 0.094 | 0.05 | 0.11 | 0.021 | 0.029 |
| BSS-PC006 | 0.073 | 0.092 | 0.125 | 0.089 | 0.076 | 0.034 | 0.055 |
| BSS-PC007 | 0.036 | 0.091 | 0.096 | 0.072 | 0.055 | 0.029 | 0.027 |
| BSS-PC008 | 0.055 | 0.101 | 0.107 | 0.059 | 0.089 | 0.038 | 0.051 |
| BSS-PC009 | 0.071 | 0.085 | 0.081 | 0.068 | 0.092 | 0.043 | 0.058 |
| BSS-PC010 | 0.067 | 0.061 | 0.086 | 0.053 | 0.069 | 0.039 | 0.033 |
| BSS-PC011 | 0.04 | 0.052 | 0.047 | 0.061 | 0.049 | 0.042 | 0.039 |
| BSS-PC012 | 0.049 | 0.046 | 0.064 | 0.063 | 0.083 | 0.031 | 0.043 |
| BSS-PC013 | 0.048 | 0.093 | 0.057 | 0.072 | 0.101 | 0.028 | 0.038 |
| BSS-PC014 | 0.073 | 0.05 | 0.057 | 0.045 | 0.061 | 0.036 | 0.047 |
| BSS-PC015 | 0.057 | 0.079 | 0.093 | 0.072 | 0.091 | 0.046 | 0.032 |
| BSS-PC016 | 0.039 | 0.043 | 0.051 | 0.042 | 0.044 | 0.032 | 0.041 |
| BSS-PC017 | 0.083 | 0.082 | 0.063 | 0.055 | 0.072 | 0.036 | 0.053 |
| BSS-PC018 | 0.074 | 0.077 | 0.085 | 0.06 | 0.095 | 0.028 | 0.035 |
| BSS-PC019 | 0.071 | 0.083 | 0.064 | 0.052 | 0.073 | 0.038 | 0.046 |
| BSS-PC020 | 0.061 | 0.072 | 0.093 | 0.051 | 0.085 | 0.035 | 0.057 |
| BSS-PC021 | 0.079 | 0.093 | 0.118 | 0.065 | 0.106 | 0.049 | 0.055 |
| BSS-PC022 | 0.07 | 0.088 | 0.083 | 0.065 | 0.081 | 0.052 | 0.059 |
| BSS-PC023 | 0.042 | 0.057 | 0.043 | 0.43 | 0.052 | 0.03 | 0.039 |
| BSS-PC024 | 0.053 | 0.051 | 0.049 | 0.041 | 0.05 | 0.021 | 0.037 |
| BSS-PC025 | 0.057 | 0.082 | 0.053 | 0.064 | 0.091 | 0.043 | 0.058 |
| BSS-PC026 | 0.032 | 0.055 | 0.072 | 0.03 | 0.073 | 0.02 | 0.031 |
| BSS-PC027 | 0.063 | 0.069 | 0.092 | 0.047 | 0.081 | 0.04 | 0.049 |
| BSS-PC028 | 0.05 | 0.051 | 0.055 | 0.039 | 0.066 | 0.031 | 0.035 |
| BSS-PC029 | 0.035 | 0.064 | 0.066 | 0.036 | 0.052 | 0.019 | 0.034 |
| BSS-PC030 | 0.037 | 0.083 | 0.065 | 0.047 | 0.091 | 0.022 | 0.037 |
| BSS-PC031 | 0.042 | 0.109 | 0.094 | 0.037 | 0.049 | 0.023 | 0.027 |
| BSS-PC032 | 0.026 | 0.068 | 0.057 | 0.061 | 0.052 | 0.029 | 0.025 |
| BSS-PC033 | 0.051 | 0.076 | 0.067 | 0.033 | 0.042 | 0.017 | 0.029 |
| BSS-PC034 | 0.023 | 0.037 | 0.039 | 0.031 | 0.027 | 0.018 | 0.023 |
| BSS-PC035 | 0.032 | 0.086 | 0.079 | 0.041 | 0.033 | 0.027 | 0.016 |
| BSS-PC036 | 0.028 | 0.09 | 0.072 | 0.036 | 0.058 | 0.025 | 0.039 |
| BSS-PC037 | 0.029 | 0.061 | 0.086 | 0.053 | 0.029 | 0.016 | 0.023 |
| BSS-PC038 | 0.039 | 0.058 | 0.064 | 0.043 | 0.066 | 0.033 | 0.045 |
| BSS-PC039 | 0.052 | 0.071 | 0.062 | 0.046 | 0.043 | 0.022 | 0.029 |
| BSS-PC040 | 0.036 | 0.049 | 0.042 | 0.037 | 0.029 | 0.021 | 0.038 |
| BSS-PC041 | 0.029 | 0.032 | 0.04 | 0.032 | 0.03 | 0.015 | 0.026 |
| BSS-PC042 | 0.034 | 0.073 | 0.072 | 0.043 | 0.081 | 0.038 | 0.038 |
| BSS-PC043 | 0.045 | 0.083 | 0.092 | 0.069 | 0.051 | 0.029 | 0.036 |
| BSS-PC044 | 0.041 | 0.042 | 0.034 | 0.053 | 0.04 | 0.02 | 0.038 |
| BSS-PC045 | 0.079 | 0.117 | 0.09 | 0.058 | 0.086 | 0.052 | 0.064 |
| BSS-PC046 | 0.071 | 0.085 | 0.083 | 0.061 | 0.074 | 0.045 | 0.042 |
| BSS-PC047 | 0.066 | 0.079 | 0.068 | 0.055 | 0.063 | 0.042 | 0.05 |
| BSS-PC048 | 0.042 | 0.047 | 0.051 | 0.034 | 0.06 | 0.033 | 0.036 |
| BSS-PC049 | 0.035 | 0.057 | 0.074 | 0.042 | 0.055 | 0.029 | 0.031 |
| BSS-PC050 | 0.039 | 0.068 | 0.052 | 0.033 | 0.087 | 0.032 | 0.041 |
| BSS-PC051 | 0.051 | 0.042 | 0.04 | 0.031 | 0.039 | 0.027 | 0.033 |
| BSS-PC052 | 0.029 | 0.044 | 0.039 | 0.04 | 0.057 | 0.024 | 0.029 |
| BSS-PC053 | 0.025 | 0.031 | 0.030 | 0.034 | 0.043 | 0.022 | 0.022 |
| BSS-PC054 | 0.033 | 0.057 | 0.046 | 0.049 | 0.052 | 0.03 | 0.039 |
| BSS-PC055 | 0.05 | 0.088 | 0.09 | 0.061 | 0.082 | 0.041 | 0.047 |
| BSS-PC056 | 0.047 | 0.039 | 0.042 | 0.039 | 0.073 | 0.033 | 0.044 |
| BSS-PC057 | 0.053 | 0.064 | 0.060 | 0.031 | 0.069 | 0.051 | 0.037 |
| BSS-PC058 | 0.042 | 0.075 | 0.071 | 0.069 | 0.082 | 0.043 | 0.052 |

-continued

| Drug number | A549 | HepG2 | TE-1 | MKN-45 | HCT116 | RPMI8226 | CFPAC-1 |
|---|---|---|---|---|---|---|---|
| BSS-PC059 | 0.043 | 0.092 | 0.099 | 0.047 | 0.086 | 0.035 | 0.046 |
| BSS-PC060 | 0.031 | 0.101 | 0.085 | 0.078 | 0.097 | 0.038 | 0.031 |
| BSS-PC061 | 0.057 | 0.122 | 0.103 | 0.065 | 0.087 | 0.033 | 0.045 |
| BSS-PC062 | 0.046 | 0.058 | 0.049 | 0.039 | 0.047 | 0.023 | 0.034 |
| BSS-PC063 | 0.069 | 0.09 | 0.083 | 0.062 | 0.109 | 0.04 | 0.046 |
| BSS-PC064 | 0.049 | 0.044 | 0.067 | 0.041 | 0.058 | 0.031 | 0.037 |
| BSS-PC065 | 0.061 | 0.052 | 0.056 | 0.035 | 0.067 | 0.029 | 0.036 |
| BSS-PC066 | 0.038 | 0.083 | 0.08 | 0.046 | 0.041 | 0.033 | 0.03 |
| BSS-PC067 | 0.037 | 0.043 | 0.047 | 0.039 | 0.055 | 0.027 | 0.035 |
| BSS-PC068 | 0.042 | 0.059 | 0.053 | 0.048 | 0.053 | 0.032 | 0.041 |
| BSS-PC069 | 0.049 | 0.068 | 0.087 | 0.042 | 0.079 | 0.036 | 0.039 |
| BSS-PC070 | 0.055 | 0.089 | 0.065 | 0.046 | 0.083 | 0.037 | 0.035 |
| BSS-PC071 | 0.075 | 0.153 | 0.106 | 0.065 | 0.072 | 0.049 | 0.061 |
| BSS-PC072 | 0.064 | 0.098 | 0.092 | 0.043 | 0.092 | 0.041 | 0.047 |
| BSS-PC073 | 0.052 | 0.061 | 0.066 | 0.059 | 0.072 | 0.031 | 0.042 |
| BSS-PC074 | 0.054 | 0.075 | 0.085 | 0.063 | 0.082 | 0.029 | 0.038 |
| BSS-PC075 | 0.043 | 0.051 | 0.049 | 0.034 | 0.057 | 0.02 | 0.031 |
| BSS-PC076 | 0.033 | 0.042 | 0.046 | 0.045 | 0.053 | 0.026 | 0.029 |
| BSS-PC077 | 0.031 | 0.033 | 0.037 | 0.034 | 0.041 | 0.018 | 0.031 |
| BSS-PC078 | 0.059 | 0.067 | 0.071 | 0.061 | 0.058 | 0.041 | 0.044 |
| BSS-PC079 | 0.069 | 0.082 | 0.073 | 0.064 | 0.071 | 0.051 | 0.053 |
| BSS-PC080 | 0.066 | 0.083 | 0.062 | 0.064 | 0.075 | 0.042 | 0.051 |
| BSS-PC081 | 0.061 | 0.069 | 0.065 | 0.061 | 0.057 | 0.039 | 0.042 |

$IC_{50}$: unit μM

What is claimed is:

1. A pyridinylcyanoguanidine derivative or a pharmaceutically acceptable salt thereof; wherein the pyridinylcyanoguanidine derivative has a structure of formula (1), (2), (3) or (4):

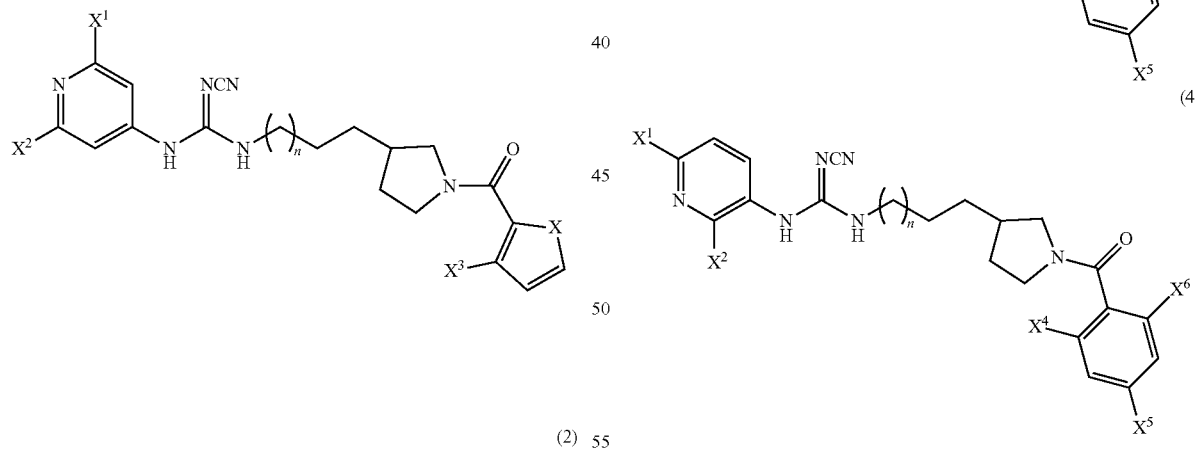

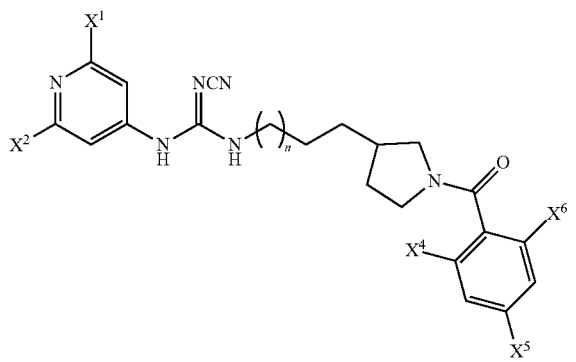

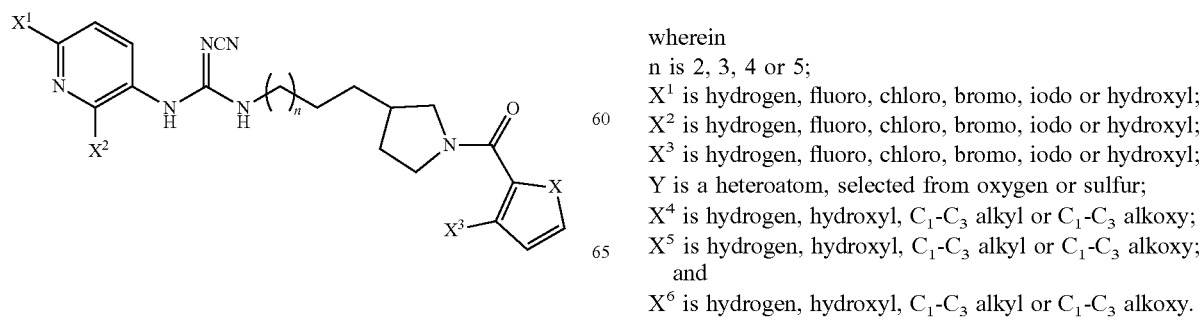

wherein
n is 2, 3, 4 or 5;
$X^1$ is hydrogen, fluoro, chloro, bromo, iodo or hydroxyl;
$X^2$ is hydrogen, fluoro, chloro, bromo, iodo or hydroxyl;
$X^3$ is hydrogen, fluoro, chloro, bromo, iodo or hydroxyl;
Y is a heteroatom, selected from oxygen or sulfur;
$X^4$ is hydrogen, hydroxyl, $C_1$-$C_3$ alkyl or $C_1$-$C_3$ alkoxy;
$X^5$ is hydrogen, hydroxyl, $C_1$-$C_3$ alkyl or $C_1$-$C_3$ alkoxy; and
$X^6$ is hydrogen, hydroxyl, $C_1$-$C_3$ alkyl or $C_1$-$C_3$ alkoxy.

2. The pyridinylcyanoguanidine derivative or a pharmaceutically acceptable salt thereof according to claim 1, wherein the pyridinylcyanoguanidine derivative has a structure selected from the group consisting of:
BSS-PC028
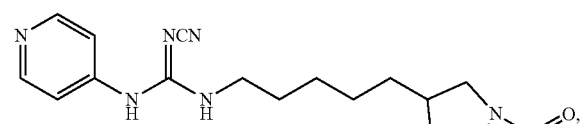
BSS-PC029
BSS-PC032
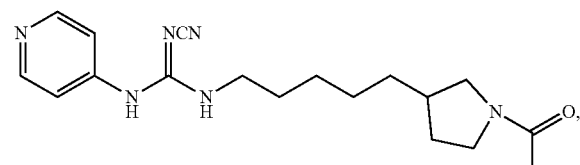
BSS-PC038
BSS-PC040
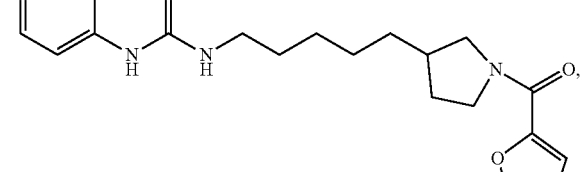
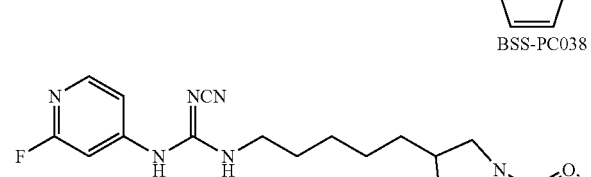
BSS-PC042
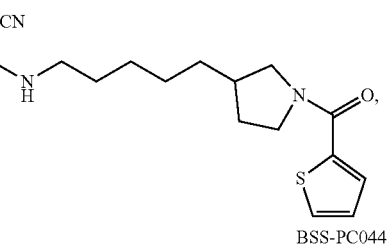
BSS-PC044
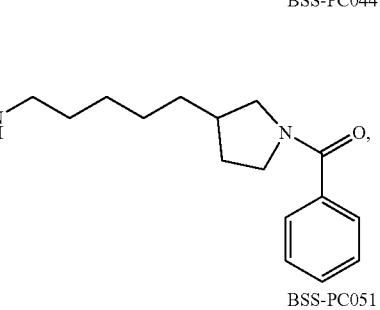
BSS-PC051
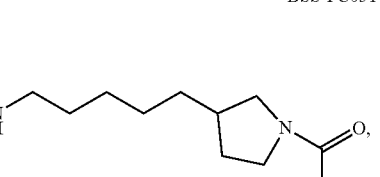
BSS-PC053
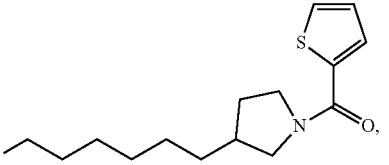
BSS-PC054
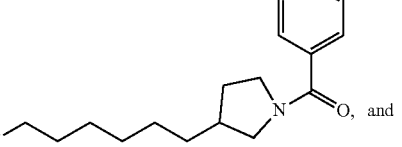
BSS-PC057
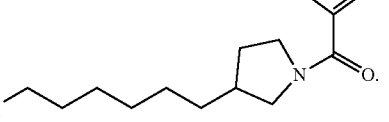
* * * * *